(12) United States Patent
Barner

(10) Patent No.: US 10,369,354 B2
(45) Date of Patent: Aug. 6, 2019

(54) SYSTEMS AND METHOD FOR ANCHORING A LEAD FOR NEUROSTIMULATION OF A TARGET ANATOMY

(71) Applicant: Boston Scientific Neuromodulation Corporation, Valencia, CA (US)

(72) Inventor: Paul Keith Barner, Waltham, MA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 134 days.

(21) Appl. No.: 15/596,761

(22) Filed: May 16, 2017

(65) Prior Publication Data

US 2017/0333702 A1 Nov. 23, 2017

Related U.S. Application Data

(60) Provisional application No. 62/337,749, filed on May 17, 2016.

(51) Int. Cl.
*A61N 1/00* (2006.01)
*A61N 1/05* (2006.01)
(Continued)

(52) U.S. Cl.
CPC ......... *A61N 1/0558* (2013.01); *A61N 1/0551* (2013.01); *A61N 1/36057* (2013.01);
(Continued)

(58) Field of Classification Search
CPC .............. A61N 1/0558; A61N 1/36062; A61N 1/37518; A61N 1/0551; A61N 1/36057;
(Continued)

(56) References Cited

U.S. PATENT DOCUMENTS

| 376,810 A | 1/1888 | Brill |
| 612,685 A | 10/1898 | Thorp et al. |

(Continued)

FOREIGN PATENT DOCUMENTS

| AU | 2012201634 A1 | 4/2012 |
| EP | 85417 A1 | 8/1983 |

(Continued)

OTHER PUBLICATIONS

International Search Report and Written Opinion for PCT/US2017/032920 dated Oct. 24, 2017.
(Continued)

*Primary Examiner* — Lindsey G Wehrheim
(74) *Attorney, Agent, or Firm* — Lowe Graham Jones PLLC; Bruce E. Black

(57) ABSTRACT

A lead having proximal and distal ends. At the distal end, a first branch includes a first biasing member and a first insulation covering. The first biasing member is disposed within the first insulation covering, which in turn includes a first inner surface. At the distal end, a second branch includes a second biasing member and a second insulation covering. The second biasing member is disposed within the second insulation covering, which in turn includes a second inner surface. The branches define a receiving channel and a stimulation region. The biasing members are movable away from each other to receive a target anatomy through the receiving channel and biasly movable toward each other to retain the target anatomy within the stimulation region. An electrode is disposed on one or both of the inner surfaces adjacent to the stimulation region, and is operable to stimulate the target anatomy.

20 Claims, 16 Drawing Sheets

(51) Int. Cl.
- *A61N 1/375* (2006.01)
- *A61N 1/378* (2006.01)
- *A61N 1/36* (2006.01)
- *A61N 1/372* (2006.01)

(52) U.S. Cl.
CPC ..... *A61N 1/36062* (2017.08); *A61N 1/36182* (2013.01); *A61N 1/3754* (2013.01); *A61N 1/3787* (2013.01); *A61N 1/37235* (2013.01); *A61N 1/37518* (2017.08)

(58) Field of Classification Search
CPC ............ A61N 1/36182; A61N 1/37235; A61N 1/3754; A61N 1/3787
See application file for complete search history.

(56) References Cited

U.S. PATENT DOCUMENTS

| | | |
|---|---|---|
| 2,046,837 A | 7/1936 | Phillips |
| 3,333,045 A | 7/1967 | Fisher et al. |
| 3,866,615 A | 2/1975 | Hewson |
| 3,918,440 A | 11/1975 | Kraus |
| 4,141,752 A | 2/1979 | Shipko |
| 4,276,882 A | 7/1981 | Dickhudt et al. |
| 4,316,471 A | 2/1982 | Shipko et al. |
| 4,462,401 A | 7/1984 | Burgio |
| 4,632,670 A | 12/1986 | Mueller, Jr. |
| 4,764,132 A | 8/1988 | Stutz, Jr. |
| 4,858,623 A | 8/1989 | Bradshaw et al. |
| 5,036,862 A | 8/1991 | Pohndorf |
| 5,107,856 A | 4/1992 | Kristiansen et al. |
| 5,143,090 A | 9/1992 | Dutcher et al. |
| 5,158,097 A | 10/1992 | Christlieb |
| 5,217,028 A | 6/1993 | Dutcher et al. |
| 5,228,248 A | 7/1993 | Haddock |
| 5,269,809 A | 12/1993 | Hayhurst et al. |
| 5,330,477 A | 7/1994 | Cook |
| 5,370,662 A | 12/1994 | Stone et al. |
| 5,376,108 A | 12/1994 | Collins et al. |
| 5,484,445 A | 1/1996 | Knuth |
| 5,584,874 A | 12/1996 | Rugland et al. |
| 5,628,780 A | 5/1997 | Helland et al. |
| 5,738,521 A | 4/1998 | Dugot |
| 5,746,722 A | 5/1998 | Pohondorf et al. |
| 5,865,843 A | 2/1999 | Baudino |
| 5,876,431 A | 3/1999 | Spehr et al. |
| 5,895,360 A | 4/1999 | Christopherson et al. |
| 5,957,968 A | 9/1999 | Belden et al. |
| 6,104,957 A | 8/2000 | Alo et al. |
| 6,175,710 B1 | 1/2001 | Kamaji et al. |
| 6,181,969 B1 | 1/2001 | Gard |
| 6,192,279 B1 | 2/2001 | Barreras, Sr. et al. |
| 6,224,450 B1 | 5/2001 | Norton |
| 6,271,094 B1 | 8/2001 | Boyd et al. |
| 6,295,944 B1 | 10/2001 | Lovett |
| 6,360,750 B1 | 3/2002 | Gerber et al. |
| 6,364,278 B1 | 4/2002 | Lin et al. |
| 6,391,985 B1 | 5/2002 | Goode et al. |
| 6,473,654 B1 | 10/2002 | Chinn |
| 6,516,227 B1 | 2/2003 | Meadows et al. |
| 6,606,523 B1 | 8/2003 | Jenkins |
| 6,609,029 B1 | 8/2003 | Mann et al. |
| 6,609,032 B1 | 8/2003 | Woods et al. |
| 6,741,892 B1 | 5/2004 | Meadows et al. |
| 6,792,314 B2 | 9/2004 | Byers et al. |
| 6,847,849 B2 | 1/2005 | Mamo et al. |
| 6,901,287 B2 | 5/2005 | Davis et al. |
| 6,902,547 B2 | 6/2005 | Aves et al. |
| 6,978,180 B2 | 12/2005 | Tadlock |
| 6,984,145 B1 | 1/2006 | Lim |
| 7,069,083 B2 | 6/2006 | Finch et al. |
| 7,072,719 B2 | 7/2006 | Vinup et al. |
| 7,161,461 B1 | 1/2007 | Nelson |
| 7,184,841 B1 | 2/2007 | Bodner et al. |
| 7,203,548 B2 | 4/2007 | Whitehurst et al. |
| 7,235,078 B2 | 7/2007 | West, Jr. |
| 7,244,150 B1 | 7/2007 | Brase et al. |
| 7,337,005 B2 | 2/2008 | Kim et al. |
| 7,337,006 B2 | 2/2008 | Kim et al. |
| 7,343,202 B2 | 3/2008 | Mrva et al. |
| 7,402,076 B1 | 7/2008 | Lim |
| 7,437,193 B2 | 10/2008 | Parramon et al. |
| 7,447,546 B2 | 11/2008 | Kim et al. |
| 7,450,993 B2 | 11/2008 | Kim et al. |
| 7,450,997 B1 | 11/2008 | Pianca et al. |
| 7,502,651 B2 | 3/2009 | Kim et al. |
| 7,580,753 B2 | 8/2009 | Kim et al. |
| 7,596,414 B2 | 9/2009 | Whitehurst et al. |
| 7,610,102 B2 | 10/2009 | Kowalczyk |
| 7,610,103 B2 | 10/2009 | Whitehurst et al. |
| 7,672,734 B2 | 3/2010 | Anderson et al. |
| 7,761,165 B1 | 7/2010 | He et al. |
| 7,783,359 B2 | 8/2010 | Meadows |
| 7,787,960 B2 | 8/2010 | Lubenow |
| 7,792,590 B1 | 9/2010 | Pianca et al. |
| 7,809,446 B2 | 10/2010 | Meadows |
| 7,848,803 B1 | 12/2010 | Jaax et al. |
| 7,853,321 B2 | 12/2010 | Jaax et al. |
| 7,860,568 B2 | 12/2010 | Deininger et al. |
| 7,949,395 B2 | 5/2011 | Kuzma |
| 7,974,706 B2 | 7/2011 | Moffitt et al. |
| 7,993,378 B2 | 8/2011 | Foley et al. |
| 8,019,443 B2 | 9/2011 | Schleicher et al. |
| 8,082,039 B2 | 12/2011 | Kim et al. |
| 8,175,710 B2 | 5/2012 | He |
| 8,204,595 B2 | 6/2012 | Pianca et al. |
| 8,224,450 B2 | 7/2012 | Brase |
| 8,224,451 B2 | 7/2012 | Jaax et al. |
| 8,229,565 B2 | 7/2012 | Kim et al. |
| 8,229,573 B2 | 7/2012 | Chen et al. |
| 8,271,094 B1 | 9/2012 | Moffitt et al. |
| 8,295,944 B2 | 10/2012 | Howard et al. |
| 8,315,704 B2 | 11/2012 | Jaax et al. |
| 8,364,278 B2 | 1/2013 | Pianca et al. |
| 8,391,985 B2 | 3/2013 | McDonald |
| 8,483,237 B2 | 7/2013 | Zimmerman et al. |
| 8,568,462 B2 | 10/2013 | Sixto et al. |
| 8,647,346 B2 | 2/2014 | Bleich et al. |
| 8,688,232 B2 | 4/2014 | Finley et al. |
| 8,688,235 B1 | 4/2014 | Pianca et al. |
| 8,712,546 B2 | 4/2014 | Kim et al. |
| 8,718,790 B2 | 5/2014 | Pianca |
| 8,768,488 B2 | 7/2014 | Barker |
| 8,774,926 B2 | 7/2014 | Alataris et al. |
| 8,831,742 B2 | 9/2014 | Pianca et al. |
| 8,849,422 B2 | 9/2014 | Pianca |
| 8,897,893 B2 | 11/2014 | Pianca |
| 8,983,624 B2 | 3/2015 | Imran |
| 9,089,694 B2 | 7/2015 | Pianca |
| 9,199,074 B2 | 12/2015 | Pianca |
| 9,205,259 B2 | 12/2015 | Kim et al. |
| 9,205,260 B2 | 12/2015 | Kim et al. |
| 9,259,569 B2 | 2/2016 | Brounstein et al. |
| 2001/0000187 A1 | 4/2001 | Peckham et al. |
| 2002/0107554 A1 | 8/2002 | Biggs et al. |
| 2003/0074023 A1 | 4/2003 | Kaplan et al. |
| 2003/0078623 A1 | 4/2003 | Weinberg et al. |
| 2003/0208247 A1 | 11/2003 | Spinelli et al. |
| 2004/0059392 A1 | 3/2004 | Parramon et al. |
| 2005/0033374 A1 | 2/2005 | Gerber |
| 2005/0033393 A1 | 2/2005 | Daglow |
| 2005/0165465 A1 | 7/2005 | Pianca et al. |
| 2005/0240238 A1 | 10/2005 | Mamo et al. |
| 2005/0283202 A1 | 12/2005 | Gellman |
| 2005/0288760 A1 | 12/2005 | Machado et al. |
| 2006/0127158 A1 | 6/2006 | Olson et al. |
| 2006/0161235 A1 | 7/2006 | King |
| 2006/0173520 A1 | 8/2006 | Olson |
| 2006/0205995 A1 | 9/2006 | Browning |
| 2006/0206162 A1 | 9/2006 | Wahlstrand et al. |
| 2007/0010794 A1 | 1/2007 | Dann et al. |
| 2007/0050005 A1 | 3/2007 | Lauro |
| 2007/0078399 A1 | 4/2007 | Olson |
| 2007/0100348 A1 | 5/2007 | Cauthen et al. |

(56) References Cited

U.S. PATENT DOCUMENTS

| | | |
|---|---|---|
| 2007/0150036 A1 | 6/2007 | Anderson |
| 2007/0219595 A1 | 9/2007 | He |
| 2007/0239248 A1 | 10/2007 | Hastings et al. |
| 2007/0255369 A1 | 11/2007 | Bonde et al. |
| 2007/0265682 A1 | 11/2007 | Wiegnann et al. |
| 2008/0071320 A1 | 3/2008 | Brase |
| 2008/0091255 A1 | 4/2008 | Caparso et al. |
| 2008/0140130 A1 | 6/2008 | Chan et al. |
| 2008/0140152 A1* | 6/2008 | Imran .................. A61N 1/0553 607/46 |
| 2008/0140153 A1 | 6/2008 | Burdulis |
| 2008/0140169 A1 | 6/2008 | Imran |
| 2008/0172116 A1 | 7/2008 | Mrva et al. |
| 2008/0183241 A1 | 7/2008 | Bedenbaugh |
| 2008/0183253 A1 | 7/2008 | Bly |
| 2008/0196939 A1 | 8/2008 | Lubenow et al. |
| 2008/0228251 A1 | 9/2008 | Hill |
| 2008/0243220 A1 | 10/2008 | Barker |
| 2008/0262588 A1 | 10/2008 | Zarembo et al. |
| 2008/0275401 A1 | 11/2008 | Sage et al. |
| 2008/0312712 A1 | 12/2008 | Penner |
| 2009/0018601 A1 | 1/2009 | Deininger et al. |
| 2009/0112272 A1 | 4/2009 | Schleicher et al. |
| 2009/0187222 A1 | 7/2009 | Barker |
| 2009/0198312 A1 | 8/2009 | Barker |
| 2009/0204193 A1 | 8/2009 | Kokones et al. |
| 2009/0210043 A1 | 8/2009 | Reddy |
| 2009/0248095 A1 | 10/2009 | Schleicher et al. |
| 2009/0254151 A1 | 10/2009 | Anderson et al. |
| 2009/0259260 A1 | 10/2009 | Bentley et al. |
| 2009/0270940 A1 | 10/2009 | Deininger |
| 2009/0276021 A1 | 11/2009 | Meadows et al. |
| 2009/0276025 A1 | 11/2009 | Burnes et al. |
| 2009/0281571 A1 | 11/2009 | Weaver et al. |
| 2009/0281576 A1 | 11/2009 | Weaver et al. |
| 2009/0281579 A1 | 11/2009 | Weaver et al. |
| 2010/0076535 A1 | 3/2010 | Pianca et al. |
| 2010/0094425 A1 | 4/2010 | Bentley et al. |
| 2010/0137938 A1 | 6/2010 | Kishawi et al. |
| 2010/0174240 A1 | 7/2010 | Wells et al. |
| 2010/0179562 A1 | 7/2010 | Linker et al. |
| 2010/0241179 A1 | 9/2010 | Gielen et al. |
| 2010/0249875 A1 | 9/2010 | Kishawi et al. |
| 2010/0268298 A1 | 10/2010 | Moffitt et al. |
| 2010/0274336 A1 | 10/2010 | Nguyen-Stella et al. |
| 2010/0286670 A1 | 11/2010 | Doyle et al. |
| 2010/0312319 A1 | 12/2010 | Barker |
| 2011/0004267 A1 | 1/2011 | Meadows |
| 2011/0005069 A1 | 1/2011 | Pianca |
| 2011/0022066 A1 | 1/2011 | Sevrain |
| 2011/0022142 A1 | 1/2011 | Barker et al. |
| 2011/0060395 A1 | 3/2011 | Cantlon |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0178573 A1 | 7/2011 | Nguyen-Stella et al. |
| 2011/0213445 A1 | 9/2011 | Blischak |
| 2011/0238129 A1 | 9/2011 | Moffitt et al. |
| 2011/0264180 A1 | 10/2011 | Hamilton |
| 2011/0276056 A1 | 11/2011 | Grigsby et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0101326 A1 | 4/2012 | Simon et al. |
| 2012/0150202 A1 | 6/2012 | Chen et al. |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232626 A1 | 9/2012 | Daglow |
| 2012/0277670 A1 | 11/2012 | Goetz |
| 2012/0283835 A1 | 11/2012 | Bentley et al. |
| 2012/0316615 A1 | 12/2012 | DiGiore et al. |
| 2012/0330355 A1 | 12/2012 | Finley et al. |
| 2013/0096659 A1 | 4/2013 | Ranu |
| 2013/0105071 A1 | 5/2013 | DiGiore et al. |
| 2013/0149031 A1 | 6/2013 | Changsrivong |
| 2013/0197424 A1 | 8/2013 | Bedenbaugh |
| 2013/0197602 A1 | 8/2013 | Pianca et al. |
| 2013/0204336 A1 | 8/2013 | Sharma |
| 2013/0238023 A1 | 9/2013 | Wales et al. |
| 2013/0261684 A1 | 10/2013 | Howard |
| 2013/0317518 A1 | 11/2013 | Govea |
| 2013/0317583 A1 | 11/2013 | Pianca |
| 2013/0317586 A1 | 11/2013 | Pianca |
| 2013/0317587 A1 | 11/2013 | Barker |
| 2013/0317588 A1 | 11/2013 | Howard et al. |
| 2013/0325091 A1 | 12/2013 | Pianca et al. |
| 2014/0018885 A1 | 1/2014 | Pianca |
| 2014/0039587 A1 | 2/2014 | Romero |
| 2014/0074093 A9 | 3/2014 | Nelson et al. |
| 2014/0180345 A1 | 6/2014 | Chan et al. |
| 2014/0257240 A1 | 9/2014 | Burdulis |
| 2014/0276925 A1 | 9/2014 | Alves et al. |
| 2014/0296953 A1 | 10/2014 | Pianca et al. |
| 2014/0343645 A1 | 11/2014 | Wechter |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0005856 A1 | 1/2015 | Pianca et al. |
| 2015/0018915 A1 | 1/2015 | Leven |
| 2015/0021817 A1 | 1/2015 | Romero et al. |
| 2015/0045864 A1 | 2/2015 | Howard |
| 2015/0045865 A1 | 2/2015 | Nageri et al. |
| 2015/0051674 A1 | 2/2015 | Barner et al. |
| 2015/0051675 A1 | 2/2015 | Barner |
| 2015/0066120 A1 | 3/2015 | Govea |
| 2015/0066121 A1 | 3/2015 | Govea et al. |
| 2015/0099936 A1 | 4/2015 | Burdulis et al. |
| 2015/0151113 A1 | 6/2015 | Govea et al. |
| 2015/0246216 A1 | 9/2015 | Barker |
| 2015/0343198 A1 | 12/2015 | Nageri et al. |
| 2017/0036013 A1 | 2/2017 | Leven |
| 2017/0333702 A1 | 11/2017 | Barner |
| 2018/0021569 A1 | 1/2018 | Pianca |

FOREIGN PATENT DOCUMENTS

| | | |
|---|---|---|
| EP | 0597213 A1 | 5/1994 |
| JP | H07-014681 | 3/1995 |
| JP | 2001339829 A | 12/2001 |
| WO | 1998033551 A1 | 8/1998 |
| WO | 1999/053994 | 10/1999 |
| WO | 2000/013743 A2 | 3/2000 |
| WO | 2000/064535 | 11/2000 |
| WO | 2003020365 A1 | 3/2003 |
| WO | 2003084398 A1 | 10/2003 |
| WO | 2004/054655 | 7/2004 |
| WO | 2005120203 A2 | 12/2005 |
| WO | 2006029257 A2 | 3/2006 |
| WO | 2006/086363 A2 | 8/2006 |
| WO | 2007041604 A2 | 4/2007 |
| WO | 2007/056384 A2 | 5/2007 |
| WO | 2007/083108 A2 | 7/2007 |
| WO | 2007/149994 A2 | 12/2007 |
| WO | 2008/094789 A1 | 8/2008 |
| WO | 2008101026 A1 | 8/2008 |
| WO | 2008/121708 A2 | 10/2008 |
| WO | 2010083308 A1 | 7/2010 |
| WO | 2010/126853 A1 | 11/2010 |
| WO | 2012151356 A1 | 11/2012 |
| WO | 2013112920 A1 | 8/2013 |

OTHER PUBLICATIONS

U.S. Appl. No. 15/442,414, filed Feb. 24, 2017.

(56) References Cited

OTHER PUBLICATIONS

U.S. Appl. No. 61/651,830, filed May 25, 2012.

* cited by examiner

000
SYSTEMS AND METHOD FOR ANCHORING A LEAD FOR NEUROSTIMULATION OF A TARGET ANATOMY

CROSS-REFERENCE TO RELATED APPLICATIONS

This application claims the benefit under 35 U.S.C. § 119(e) of U.S. Provisional Patent Application Ser. No. 62/337,749, filed May 17, 2016, which is incorporated herein by reference.

FIELD

The present invention is directed to the area of implantable electrical stimulation systems and methods of making and implanting the same. More specifically, the present invention is directed to systems and methods for anchoring a lead for neurostimulation of a target anatomy (e.g., the dorsal root ganglia).

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Dorsal root ganglia are nodules of cell bodies disposed along the dorsal roots of spinal nerves. Dorsal root ganglia are disposed external to the epidural space. Dorsal root ganglia, however, are disposed in proximity to the spinal cord and the vertebral column.

BRIEF SUMMARY

In at least some embodiments, an electrical stimulation lead has a proximal end and a distal end. At the distal end, the lead includes a first branch includes a first biasing member and a first insulation covering. The first biasing member is disposed within the first insulation covering, which in turn includes a first inner surface. Again at the distal end, the lead includes a second branch includes a second biasing member and a second insulation covering. The second biasing member is disposed within the second insulation covering, which in turn includes a second inner surface. The first and second branches define a receiving channel and a stimulation region proximal to the receiving channel. The first and second biasing members are movable away from each other to receive a target anatomy through the receiving channel and biasly movable toward each other to retain the target anatomy within the stimulation region. And, at least one electrode is disposed on one or both of the first inner surface or the second inner surface. The electrode is disposed adjacent to the stimulation region, and the electrode is operable to electrically stimulate the target anatomy.

In at least some other embodiments, the first and second biasing members comprise a shape memory material, and the shape memory material may be nitinol.

In at least other embodiments, at least one of the first or second biasing member is electrically coupled to at least one of the at least one electrode. In at least some other embodiments, the lead includes a plurality of conductors disposed in one or both of the first or second insulation coverings.

In at least some other embodiments, the first branch includes a first hook portion, the second branch may also include a second hook portion, and the first and second hook portions define the receiving channel.

In at least some other embodiments, an electrical stimulation system includes the lead of described above and a control module coupleable to the lead, the control module having a housing and an electronic subassembly disposed in the housing.

In at least some embodiments, an electrical stimulation lead has a proximal end and a distal end. At the distal end, the lead includes a first biasing member having a first branch and a second branch extending distally from the first branch. Again at the distal end, the lead includes a second biasing member having a third branch and a fourth branch extending distally from the third branch. The second and fourth branches are angled to define a receiving channel and a throat region with a throat width. The first and third branches define a stimulation region proximal to the receiving channel. The first and second biasing members are biasly movable away from each other to increase the throat width and receive a target anatomy through the throat region. The first and second biasing members are biasly movable toward each other to retain the target anatomy within the stimulation region. And, at least one electrode disposed on one or both of the first or second biasing members, adjacent to the stimulation region, and is operable to electrically stimulate the target anatomy.

In at least some other embodiments, the first and second biasing members comprise a shape memory material, and the shape memory material may be nitinol.

In at least some embodiments, an electrical stimulation lead has a proximal end and a distal end. The lead includes a housing located at the distal end portion of the lead. The lead includes an anchor member having a first configuration disposed within the housing. The lead includes a lumen coupled to the housing. Lastly, the lead includes an anchor actuation device extending through the lumen and directly coupled to the anchor member, such that the anchor actuation device is movable to distally urge the anchor member out of the housing into a deployed configuration in a vicinity of a target anatomy to entangle with patient tissue to secure the lead in the vicinity of the target anatomy.

In at least some other embodiments, the anchor member is made from nitinol.

In at least some other embodiments, the anchor member is a ribbon member that is helically wound when in the un-deployed configuration. In some other embodiments, the anchor member is a coil-shaped anchor member that may have a pigtail-shaped configuration when in a deployed configuration. The pigtail-shaped configuration engages a patient's tissue in a vicinity of the target anatomy for neurostimulation. The anchor actuation device is movable to retract the anchor member into an un-deployed configuration.

In at least some other embodiments, an electrical stimulation system includes the lead described above and a control module coupleable to the lead, the control module having a housing and an electronic subassembly disposed in the housing.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and implanting the same. More specifically, the present invention is directed to neurostimulation leads with conductive polymer electrodes for an electrical stimulation system and methods of making the same.

Suitable implantable electrical stimulation systems include, but are not limited to, a least one lead with one or more electrodes disposed along a distal end of the lead.

Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,203,548; 7,244,150; 7,450,997; 7,596,414; 7,610,103; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entireties. Examples of implanting or anchoring leads may be found in U.S. Pat. Nos. 8,019,443; 8,718,790; 8,768,488; 8,849,422; and U.S. Patent Publication Nos. 2012/0185027; 2013/01317518, which are incorporated by reference in their entireties.

Figure 1:
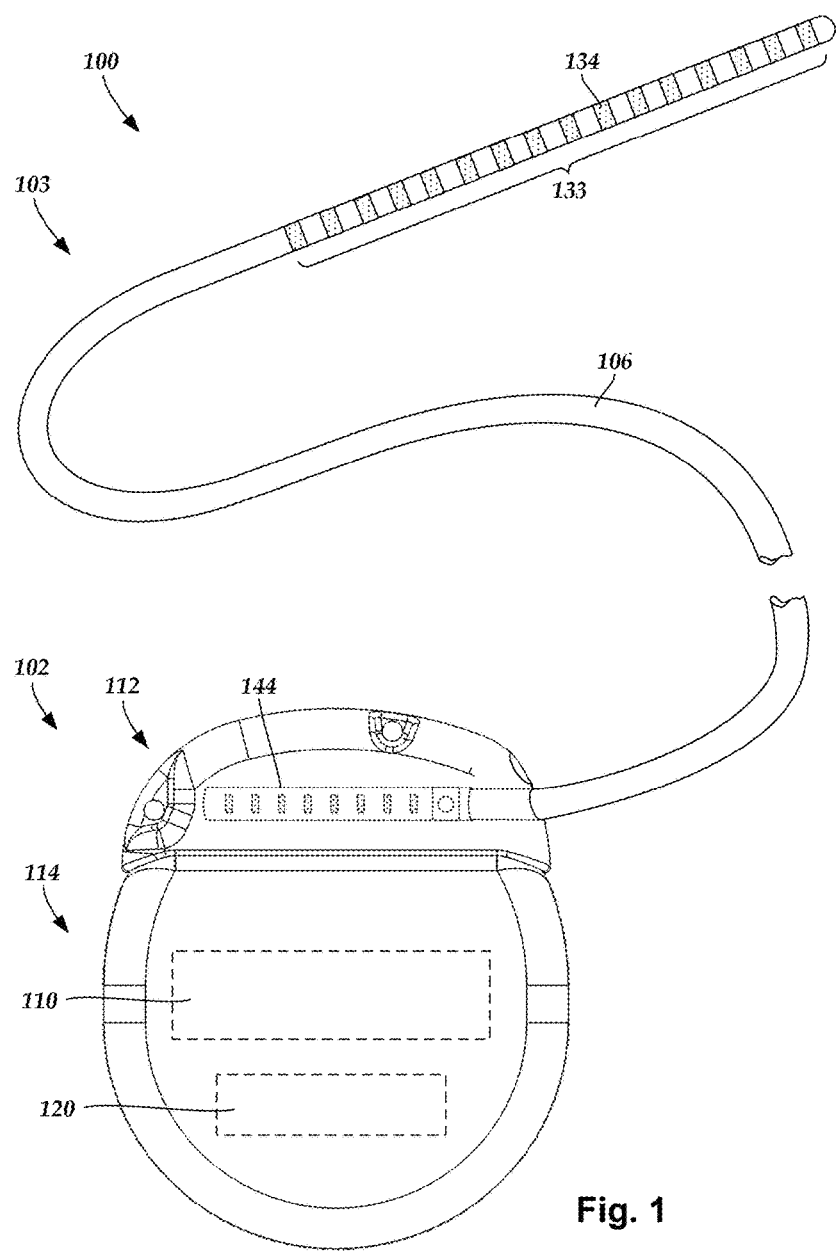
FIG. 1 is a schematic view of one embodiment of an electrical stimulation system that includes a lead electrically coupled to a control module according to an embodiment of the present invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. Stimulation circuitry 110 and an optional power source 120 are disposed in the electronics housing 114. A control module connector 144 is disposed in the connector housing 112. The control module connector 144 is configured and arranged to make an electrical connection between the lead 103 and the stimulation circuitry 110 of the control module 102.

The electrical stimulation system or components of the electrical stimulation system, including the lead body 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the lead body 106 are typically disposed in, or separated by, a non-conductive, biocompatible material such as, for example, silicone, polyurethane, polyetheretherketone ("PEEK"), epoxy, and the like or combinations thereof. The lead body 106 may be formed in the desired shape by any process including, for example, molding (including injection molding), casting, and the like. The non-conductive material typically extends from the distal end of the lead body 106 to the proximal end of the lead body 106.

Figure 2A:
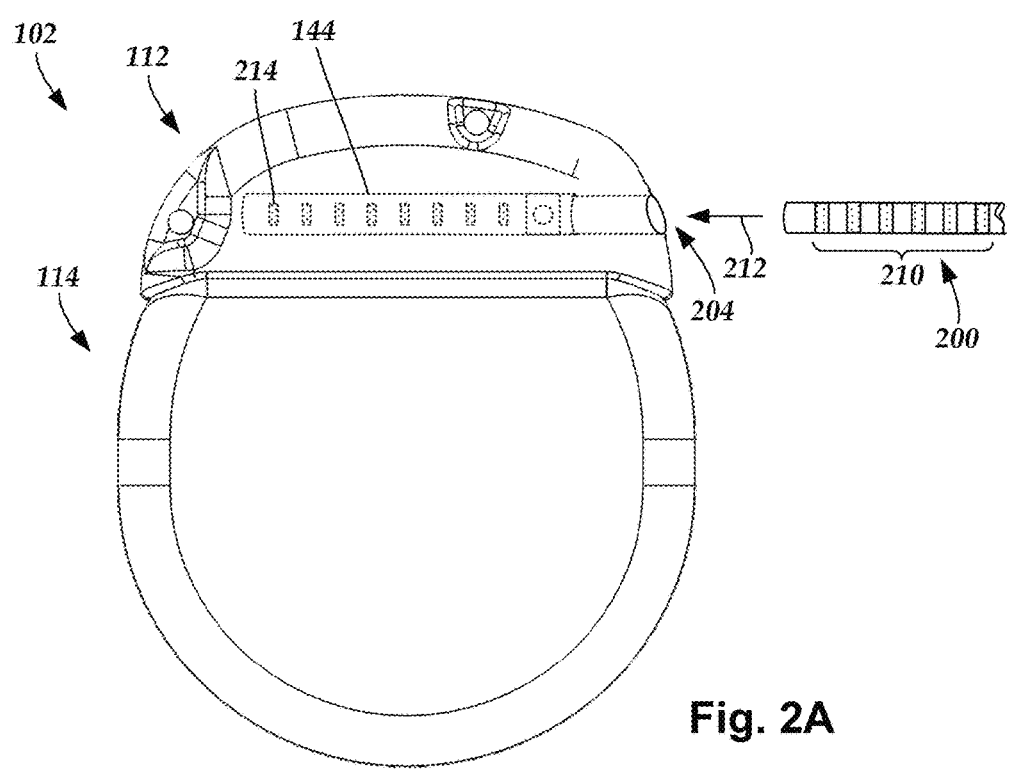
FIG. 2A is a schematic view of one embodiment of the control module of FIG. 1 configured and arranged to electrically couple to an elongated device according to an embodiment of the present invention.
Figure 2B:
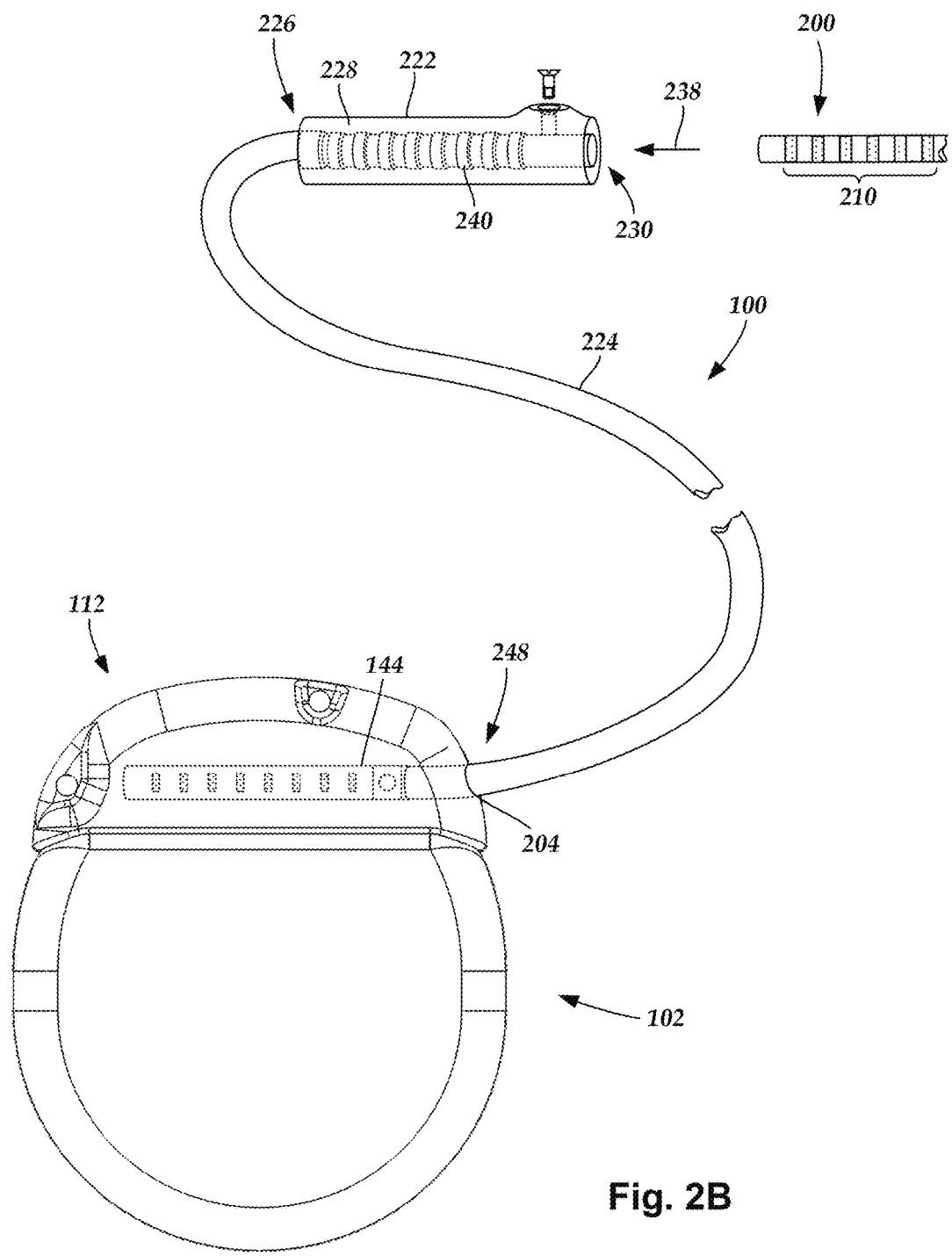
FIG. 2B is a schematic view of one embodiment of a lead extension configured and arranged to electrically couple the elongated device of FIG. 2A to the control module of FIG. 1 according to an embodiment of the present invention.

Terminals (e.g., 210 in FIGS. 2A-2B) are typically disposed along the proximal end of the lead body 106 of the electrical stimulation system 100 (as well as any splitters, lead extensions, adaptors, or the like) for electrical connection to corresponding connector contacts (e.g., 214 and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the lead body 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the lead extension 224 of FIG. 2B, an adaptor, or the like or combinations thereof), or a combination thereof.

The control module connector 144 defines at least one port into which a proximal end of the elongated device 200 can be inserted, as shown by directional arrow 212. In FIG. 2A (and in other figures), the connector housing 112 is shown having one port 204. The connector housing 112 can define any suitable number of ports including, for example, one, two, three, four, five, six, seven, eight, or more ports.

The control module connector 144 also includes a plurality of connector contacts, such as connector contact 214, disposed within each port 204. When the elongated device 200 is inserted into the port 204, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

In at least some instances, a large control module, such as the control module 102 illustrated in FIGS. 1-2B, is not desirable. A smaller, more compact control module may be suitable for situations such as, for example, short-term implantation (for example, 1 or 2 weeks, 1, 2, 3, 4, 6, 8, 12, or 18 months), short-term trial (for example, 1 or 2 weeks, 1, 2, 3, 4, 6, 8, 12, or 18 months), clinical studies (for example, for a period of 1 or 2 weeks, 1, 2, 3, 4, 6, 8, 12, or 18 months), or the like. Such a control module may also be useful when a less invasive surgical implantation is desired, recommended, or required. In some instances, a patient or clinician may be willing to charge the control module more frequently if the control module is smaller or the surgery is less invasive. In addition, there may be more options in the body of the patient for implantation of a smaller control module than are available for the larger control module (which is often implanted in the thoracic body cavity or the buttocks due to the size of the device.) A smaller control module may also be less expensive and particularly useful for trials to determine whether electrical stimulation is beneficial. In at least some embodiments, the electrical stimulation system with the smaller control module can be upgraded to an electrical stimulation system such as that illustrated in FIGS. 1-2B if the trial shows sufficient benefit to the patient. In at least some embodiments, the smaller control module may allow for the device to be MRI (magnetic resonance imaging) conditionally safe because of its implant location and size.

In some embodiments, the control module can be made smaller by permanently affixing the lead (or a lead extension) to the control module. For example, the lead can be hardwired to the stimulation circuitry so that the control module does not need a connector and header.

Figure 3A:
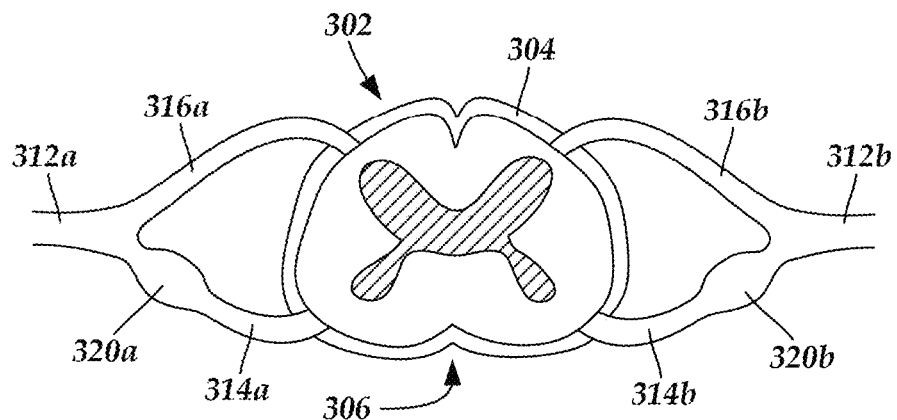
FIG. 3A is a schematic transverse cross-sectional view of spinal nerves extending from a spinal cord, the spinal nerves including dorsal root ganglia.

FIG. 3A schematically illustrates a transverse cross-sectional view of a spinal cord 302 surrounded by dura 304. The spinal cord 302 includes a midline 306 and a plurality of levels from which spinal nerves 312a and 312b extend. In at least some spinal cord levels, the spinal nerves 312a and 312b extend bilaterally from the midline 306 of the spinal cord 302. In FIG. 3A, the spinal nerves 312a and 312b are shown attaching to the spinal cord 302 at a particular spinal cord level via corresponding dorsal roots 314a and 314b and corresponding ventral (or anterior) roots 316a and 316b. Typically, the dorsal roots 314a and 314b relay sensory information into the spinal cord 302 and the ventral roots 316a and 316b relay motor information outward from the spinal cord 302. One or more dorsal root ganglia ("DRG") 320a and 320b are nodules of cell bodies that are disposed along the dorsal roots 316a and 316b in proximity to the spinal cord 302.

Figure 3B:
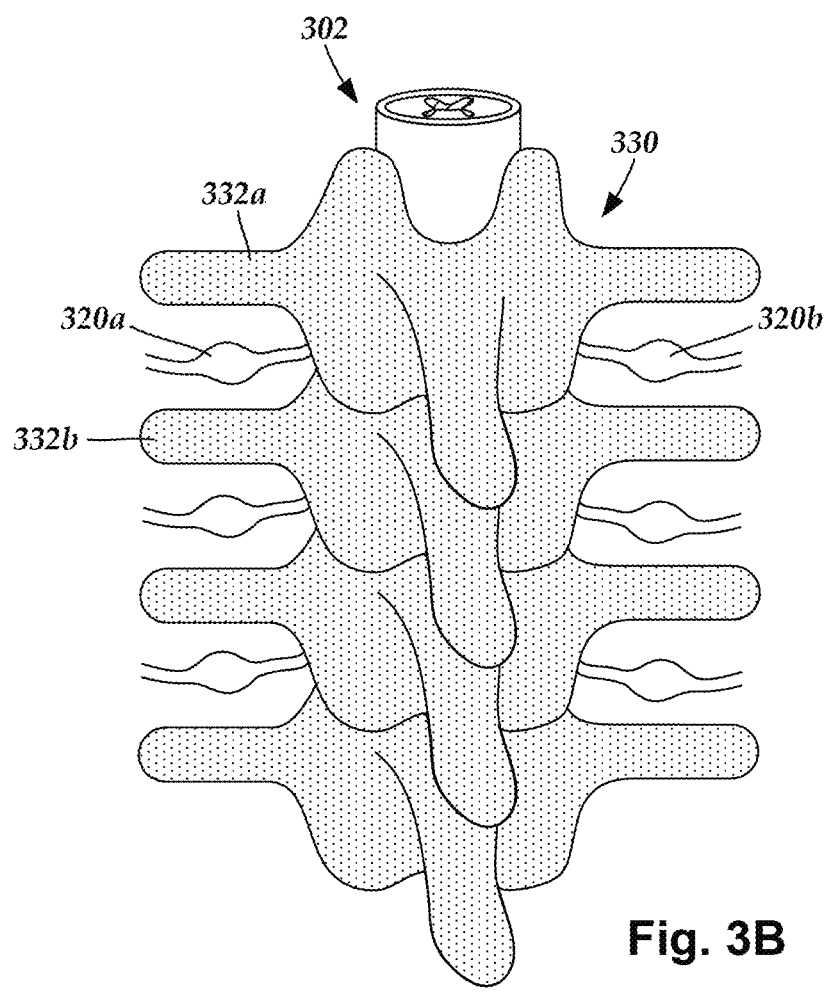
FIG. 3B is a schematic perspective view of a portion of the spinal cord of FIG. 3A disposed in a portion of a vertebral column with the dorsal root ganglia of FIG. 3A extending outward from the vertebral column.

FIG. 3B schematically illustrates a perspective view of a portion of the spinal cord 302 disposed along a portion of a vertebral column 330. The vertebral column 330 includes stacked vertebrae, such as vertebrae 332a and 332b, and a plurality of DRGs 320a and 320b extending outwardly bilaterally from the spinal cord 302 at different spinal cord levels. In at least some embodiments, one or more DRG are potential target stimulation locations.

The DRG is an anatomical feature that contains the cell bodies of sensory (afferent) nerves which are contained in the nerve root of the spinal cord. The cell bodies being outside of the central nervous system is due to the pseudomonopolar structure of the sensory nerves. The DRG can be a target for neurostimulation therapy due to factors such as, but not limited to, less cerebrospinal fluid, more direct contact, the DRG is less delicate than the spinal cord, the DRG comprises only sensory nerve cell bodies (no motor nerves targeted), and a potential decrease in paresthesia.

Figure 3C:
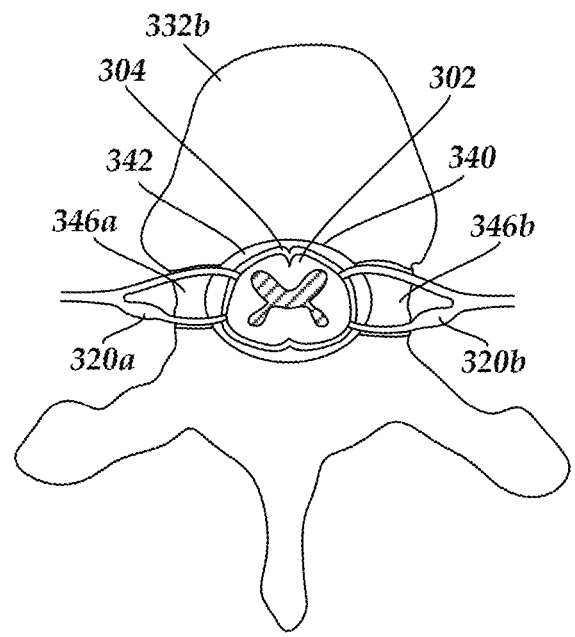
FIG. 3C is a schematic top view of a portion of the spinal cord of FIG. 3A disposed in a vertebral foramen defined in a vertebra of the vertebral column of FIG. 3B, the vertebra also defining intervertebral foramina extending between an outer surface of the vertebra and the vertebral foramen, the intervertebral foramina providing an opening through which the dorsal root ganglia of FIG. 3B can extend outward from the spinal cord of FIG. 3B.

FIG. 3C schematically illustrates a top view of a portion of the spinal cord 302 and surrounding dura 304 disposed in a vertebral foramen 340 defined in the vertebra 332b. The vertebrae, such as the vertebrae 332a and 332b, are stacked together and the vertebral foramina 340 of the vertebrae collectively form a spinal canal through which the spinal cord 302 extends. The space within the spinal canal between the dura 304 and the walls of the vertebral foramen 340 defines the epidural space 342. Intervertebral foramina 346a and 346b, defined bilaterally along sides of the vertebra 332b, form openings through the vertebra 332b between the epidural space 342 and the environment external to the vertebra 332b.

Figure 3D:
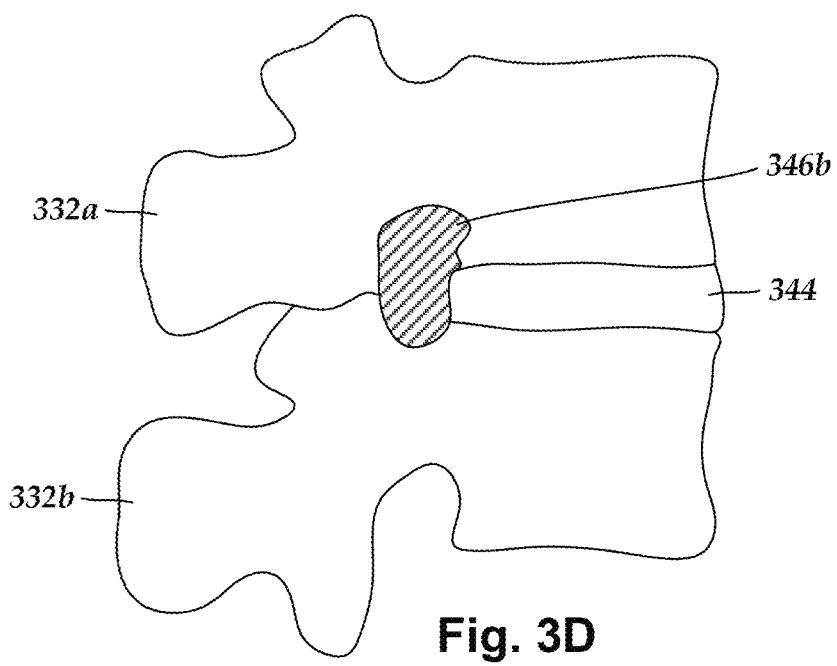
FIG. 3D is a schematic side view of two vertebrae of the vertebral column of FIG. 3B, the vertebrae defining an intervertebral foramen through which one of the dorsal root ganglia of FIG. 3B can extend outward from the spinal cord of FIG. 3B.

FIG. 3D schematically illustrates a side view of two vertebrae 332a and 332b coupled to one another by a disc 344. The intervertebral foramen 346b is shown defined between the vertebrae 332a and 332b. The intervertebral foramen 346b provides an opening for one or more of the dorsal root 314b, ventral root 316b, and DRG 320b to extend outwardly from the spinal cord 302 to the environment external to the vertebrae 332a and 332b.

Figure 4:
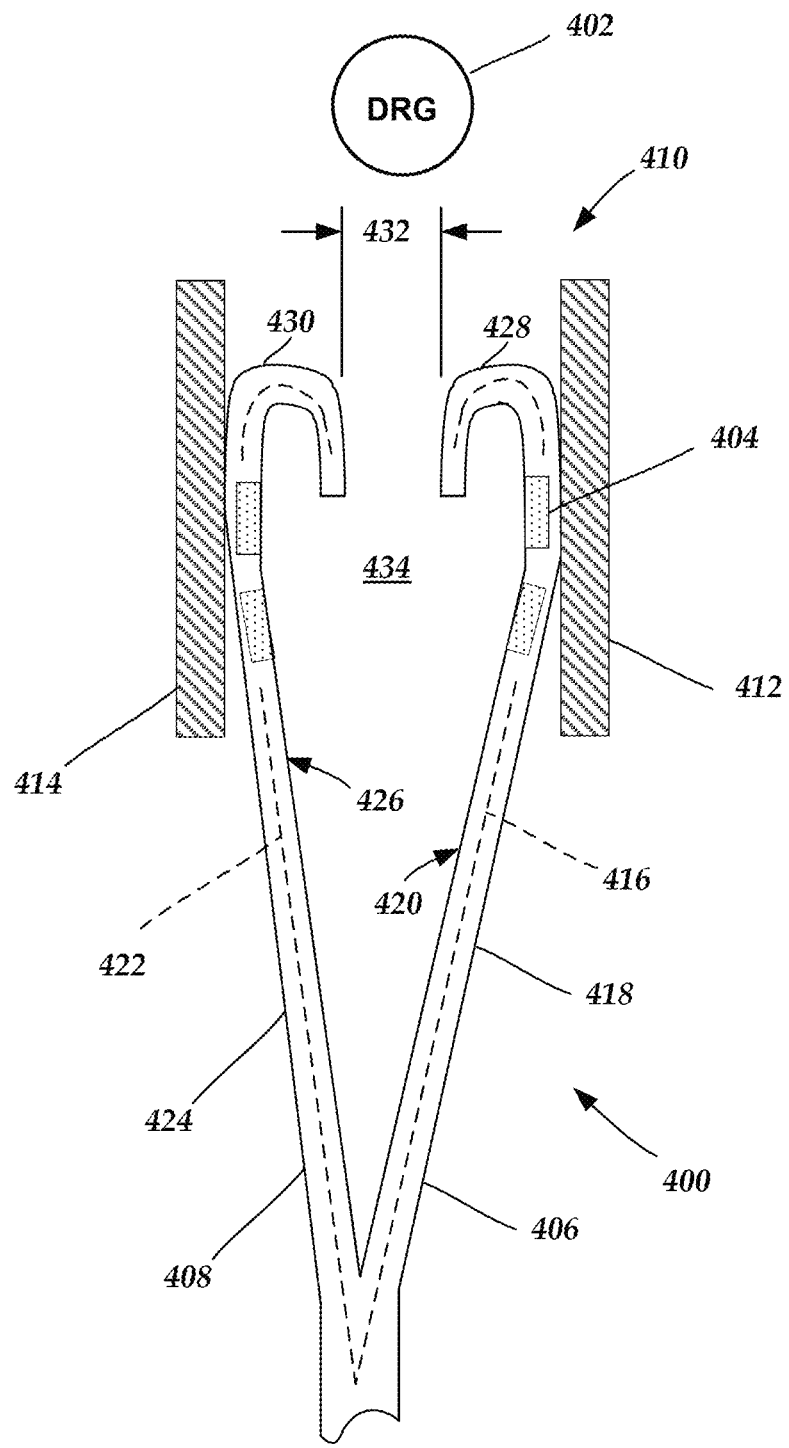
FIG. 4 is a schematic view of a distal end of a lead having biasing members configured to capture and retain a target anatomy according to an embodiment of the present invention.

FIG. 4 schematically illustrates a distal end 400 of a lead 103 (FIG. 1) in which the distal end 400 is configured for directly surrounding, encompassing, retaining or capturing a dorsal root ganglia (DRG) 402 as compared to anchoring the lead to tissue outside of an epidural space 342 (FIG. 3C) away from the distal end 400 of the lead 103. Capturing or retaining the lead 103 more directly to a target anatomy (e.g., DRG 402) could advantageously allow for more efficient and more effective therapy. In at least some embodiments and after the distal end 400 is attached to the DRG 402, one or more electrodes 404 may be controllably actuated to selectively stimulate the DRG 402. The distal end 400 can be incorporated into different types of leads such as, but not limited to, a percutaneous lead, a paddle lead or some other type of lead.

The electrodes 404 can be formed using any conductive, biocompatible material. Examples of suitable materials include metals, alloys, conductive polymers, conductive carbon, and the like, as well as combinations thereof. In at least some embodiments, one or more of the electrodes 404 are formed from one or more of: platinum, platinum iridium, palladium, palladium rhodium, or titanium. The number of electrodes 404 may vary, for example, there can be two, four, six, eight, ten, twelve, fourteen, sixteen, or more electrodes 404. As will be recognized, other numbers of electrodes 404 may also be used.

The distal end 400 includes a first branch 406 and a second branch 408 that are movable through an intervertebral foramen 410 defined between vertebrae 412 and vertebrae 414. The first and second branches 406, 408 are configured to capture and retain the DRG 402 in close proximity to the electrodes 404.

In at least some embodiments, the first branch 412 includes a first biasing member 416 disposed within a first insulation covering 418 that defines a first inner surface 420. Similarly, the second branch includes a second biasing member 422 disposed within a second insulation covering 424 that defines a second inner surface 426. The biasing members 416 and 422 are shown as dashed lines because they are disposed within the insulation coverings 418 and 424, respectively. At least one electrode may be disposed on the inner surface of at least one of the branches 406, 408.

In at least some embodiments, the biasing members 416 and 422 may be made from any conductive, biocompatible material such as, but limited to, spring wire or music wire. By way of example, the biasing members 416 and 422 may be made from stainless steel, carbon, platinum, platinum iridium, palladium, palladium rhodium, titanium aluminum, some combination thereof, or some other conductive material.

Optionally, one or both of the biasing members may function as a conductor to provide electrical communication between one or more electrodes and a proximal end of the lead. Additionally or alternatively, other conductors (not shown) may be embedded in the insulation coverings 418 and 424 or can be disposed in one or more lumens (not shown) extending along the branches 406, 408. In some embodiments, there is an individual lumen for each conductor. In other embodiments, two or more conductors extend through a lumen. In other embodiments, at least one of the conductors in each branch also functions as the biasing member. In still other embodiments, the biasing member may be non-conductive. In at least some embodiments, the biasing members 416 and 422 may be made from a shape memory material such as, but not limited to, nitinol.

In at least some embodiments, the insulation coverings 418 and 424 may be made from a non-conductive, biocompatible material such as, for example, silicone, polyurethane, polyetheretherketone ("PEEK"), epoxy, and the like or combinations thereof. The distal end 400 may be formed into a variety of shapes by any process including, for example, molding (including injection molding), casting, and the like.

The biasing members 416 and 422 and their respective insulation coverings 418 and 424 cooperate to provide the branches 406 and 408 with a desired amount of rigidity that allows the branches to move laterally relative to each other (e.g., toward or away from each other). In general, the term bias, as used herein, means a deviation from an established point of reference. Such a deviation may be achieved using spring-loaded elements, shape memory elements, interference fit components or assemblies (e.g., mechanical or thermal), or any other material, element, devise, component, assembly, system that is movable from a first position (e.g., point of reference) to a second position. The desired amount of bias may depend on one or more parameters such as, but not limited to, the material, mass, thickness, and shape of the biasing members, the insulation coverings or both. By way of example, the biasing members 416, 422 may include hook portions that face inward toward each other (as illustrated), the hook portions may be spaced apart or in contact when in a non-deployed or implantation configuration. In at least some embodiments, the hook portions may be separated by a force supplied by a tool inserted through a lumen in the lead, by a direct manipulation of the biasing members, by overcoming a threshold (e.g., temperature activation or pseudo- or super-elasticity) parameter for actuation of a shape memory material, by application of a magnetic field or electromagnetic field, etc.

In at least some embodiments, the first biasing member 416 includes a first hook portion 428 and the second biasing member 422 includes a second hook portion 430. The hook portions 428 and 430 are configured to oppose and face towards each other. In other embodiments, the one branch may have the hook portion while the other branch is generally straight or both branches may be straight (refer to description below with respect to FIG. 6).

In at least some embodiments, the branches 406, 408 define a receiving channel 432 and a stimulation region 434 located proximal to the receiving channel 432. The desired amount of rigidity of the branches 406, 408 permits the branches to be held laterally apart or actively separated so the DRG 402 can be maneuvered through the receiving channel 432. Once the DRG 402 is sufficiently within the stimulation region 434, the branches 406, 408 can bias (e.g., spring or snap) laterally toward each other to reduce the receiving channel 432 sufficient to retain or capture the DRG 402 within the stimulation region 434.

Figure 5:
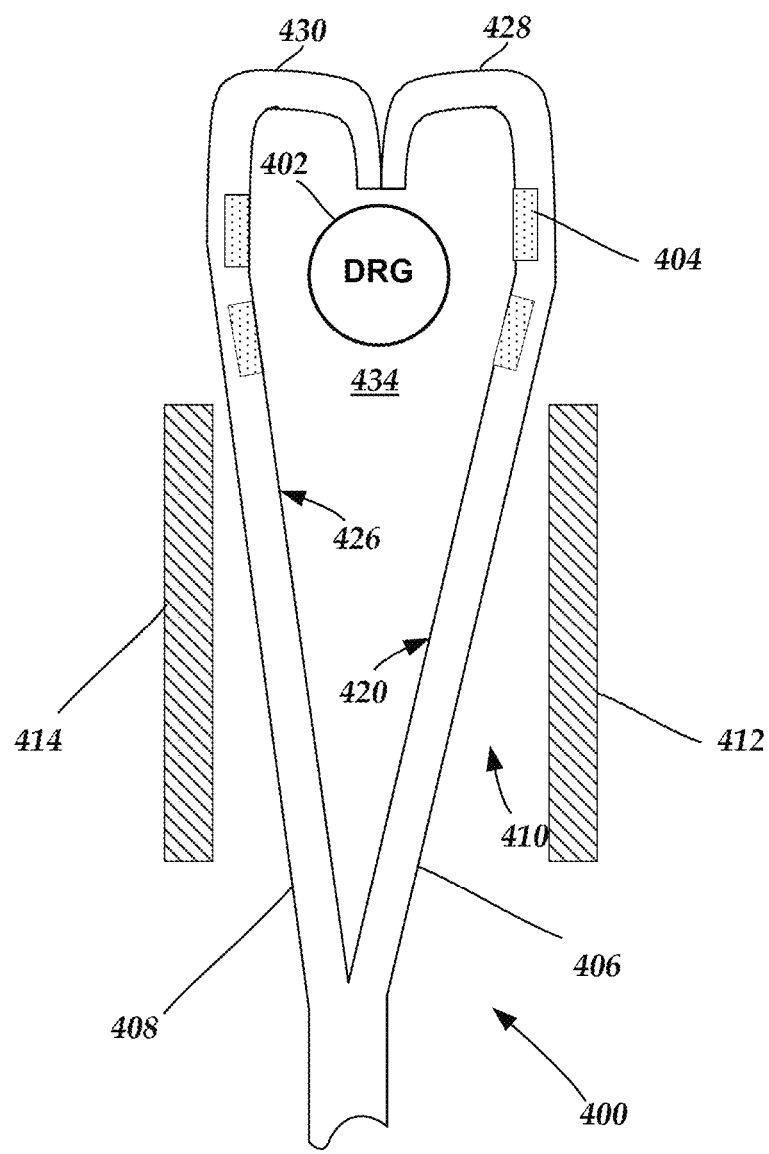
FIG. 5 is a schematic view of the distal end of a lead of FIG. 4 with the target anatomy retained within a stimulation region formed by the biasing members according to an embodiment of the present invention.

FIG. 5 shows the DRG 402 captured and retained by the branches 406 and 408. For purposes of brevity and clarity, the biasing members are not shown. The desired amount of rigidity for the branches 406 and 408 allows them to be moved past the DRG 402 without imparting an undesirable force on the DRG 402. At least one electrode 404 is disposed on one or both of the first inner surface 420 and the second inner surface 426. The illustrated embodiment shows two electrodes 404 disposed on each branch 406, 408, but a greater or lesser number of electrodes may be used. The electrodes 404 are adjacent to and face toward the stimulation region 434. The electrodes 404 are operable to controllably stimulate the DRG 402.

Figure 6:
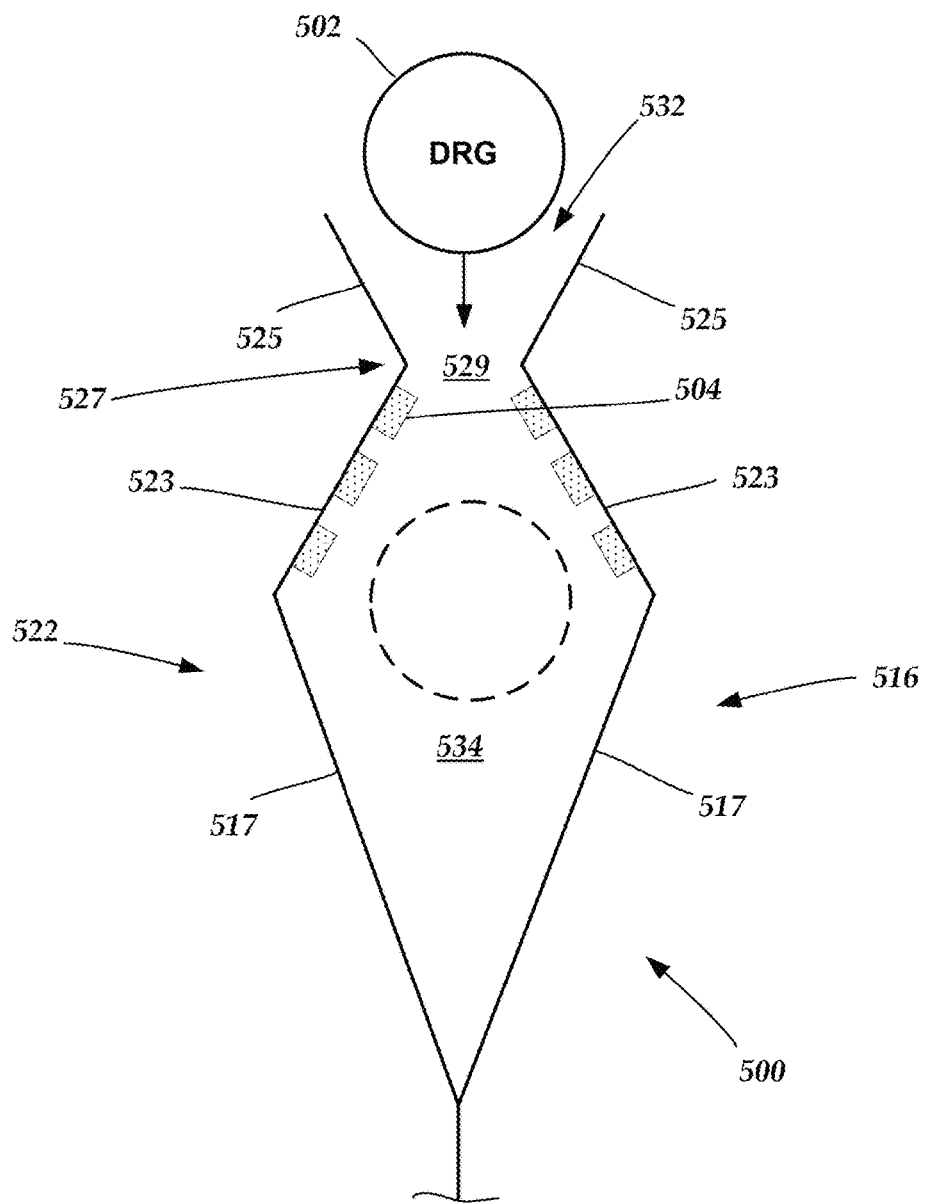
FIG. 6 is a schematic view of a distal end of a lead having biasing members configured to capture and retain a target anatomy according to an embodiment of the present invention.

FIG. 6 schematically and conceptually illustrates a distal end 500 of a lead 103 (FIG. 1). For purposes of brevity and clarity, the insulation coverings and the vertebrae defining the intervertebral foramen are not shown. The distal end 500 includes a first biasing member 516 and a second biasing member 522. Each biasing member 516, 522 includes a proximal branch 517, an intermediate branch 523, and a distal branch 525.

The distal branches 525 can be straight branches that define a receiving channel 532. The proximal and intermediate branches 517, 523 define a stimulation region 534 located proximal to the receiving channel 532. An intersection 527 between the intermediate branches 523 and the distal branches 525 takes the form of a throat region 529 that may be biasly and selectively expanded or separated to receive a DRG 502. The biasing members 516, 522 have an amount of rigidity that permits them to be held apart or actively separated when urging the intersection 527 over the DRG 502. After the DRG 502 has been received within the stimulation region 534, the biasing members 516, 522 are permitted to bias (e.g., spring or snap) relative to each other to reduce the spaced apart distance of the biasing members in a vicinity of the throat region 529. The desired amount of rigidity of the branches permits them to be held laterally apart or actively separated so the DRG 502 can be maneuvered through the receiving channel 532 or so the throat region 529 can be maneuvered over and past the DRG 502. Once the DRG 502 is sufficiently within the stimulation region 534, the branches can bias (e.g., spring or snap) laterally toward each other to reduce the spaced-apart distance of the throat region 529 by an amount sufficient to retain or capture the DRG 402 within the stimulation region 534.

In at least some embodiments, the biasing members 516, 522 are made from nitinol wire having a predetermined shape, as illustrated. Nitinol wire may be delivered into the body having one shape and then activated into another shape after implantation. In at least some embodiments, the biasing members 516, 522 may electrically couple a plurality of electrodes 504 to a proximal end of the lead.

In at least some embodiments, the distal end of the lead may be placed directly onto the DRG, placed adjacent to the DRG, may pierce one wall of a nerve root sleeve and then placed directly onto the DRG, placed between the DRG and a ventral nerve root, which may include piercing both walls of a nerve root sleeve, or placed between the ventral nerve root and a dorsal nerve root.

Figure 7:
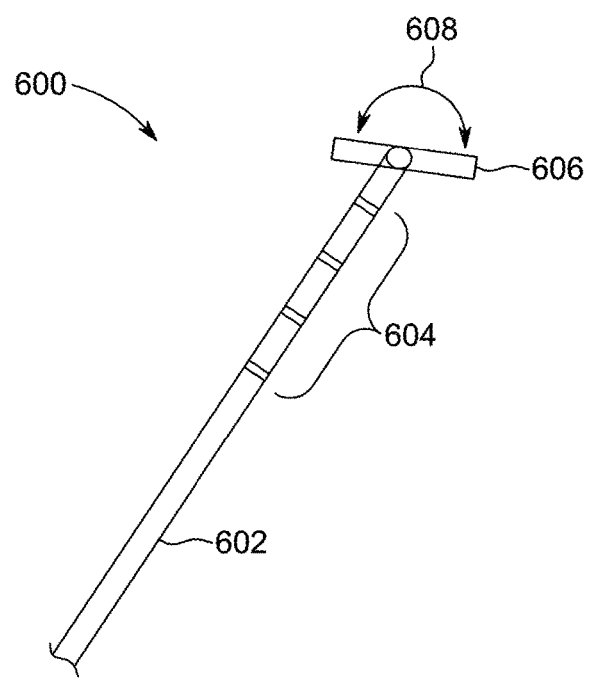
FIG. 7 is a schematic, perspective view of a distal end of a lead having a pivoting anchor according to an embodiment of the present invention.

FIG. 7 schematically illustrates a distal end 600 of a lead 103 (FIG. 1) that includes a lead body 602, a plurality of electrodes 604 and a pivoting anchor 606. In at least some embodiments, the pivoting anchor 606 may be inserted through the DRG or surrounding anatomy and anchored, for example, into the intervertebral ligaments near the DRG. During implantation, the pivoting anchor 606 may be rotated to be parallel or approximately parallel to the lead body 602. Once the pivoting anchor 606 has reached its intended destination within the patient, the pivoting anchor 606 may be rotated with a tool, stylet, or wire extending through a lumen within the lead body 602. For example, the pivoting anchor 606 can be pivoted as indicated by arrow 608 relative to the lead body 602 to be perpendicular or non-parallel to the lead body 602 to effectuate the capturing or retaining of a target anatomy (e.g., DRG) (not shown). The pivoting action may operate to embed, entwine or entangle the pivoting anchor 606 into patient tissue. Additionally or alternatively, the pivoting action may lodge the pivoting anchor 606 behind an anatomical feature such as, but not limited to, a bone passageway, a ligament, a tendon or a muscle.

Figure 8:
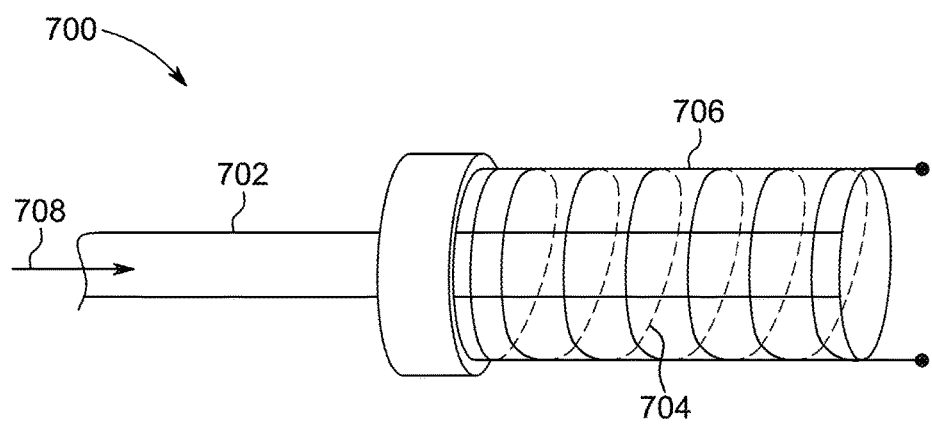
FIG. 8 is a schematic view of a distal end of a lead having a ribbon-style anchor according to an embodiment of the present invention.

FIG. 8 schematically illustrates a ribbon anchor 700 having a lumen 702 coupled to a ribbon member 704. In some embodiments, the ribbon member 704 takes the form of a helically wound (e.g., "spiral-cut") wire located within a housing 706, which may take the form of a biocompatible housing. During implantation, a stylet (shown as arrow 708) is inserted through the lumen 702 to urge the ribbon member 704 into the patient's tissue near the DRG. As the ribbon member 704 is pushed out of the housing 706 by the stylet 708, the ribbon member unwinds or uncoils to become tangled in the tissue, thereby anchoring a distal end of a lead near the DRG. The ribbon member 704 may have any number of coils and a uniform or varied pitch. In some embodiments, the ribbon member 704 may be retracted from the patient's tissue by pulling the ribbon member in a proximal direction with the stylet 708.

Figure 9A:
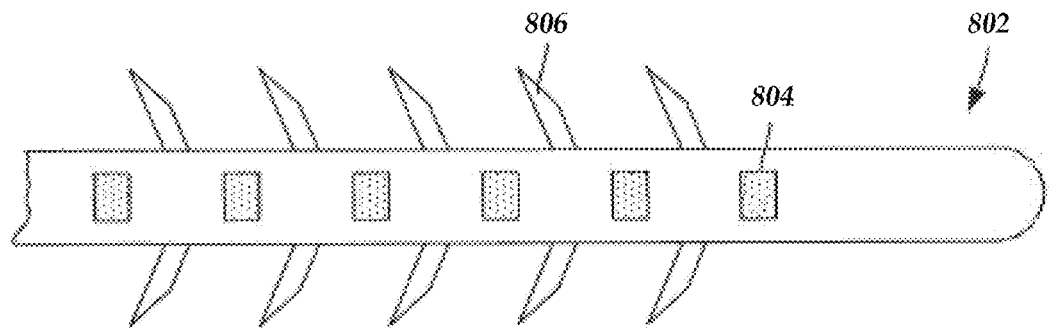
FIG. 9A is a schematic side view of one embodiment of a distal portion of a lead with barbs in deployed positions disposed between each of a plurality of electrodes, according to the invention.

In some embodiments, an anchoring unit includes one or more barbs disposed on a lead between adjacent electrodes. FIG. 9A is a schematic side view of one embodiment of a distal portion of a lead 802. The lead 802 includes a plurality of electrodes, such as electrode 804, and a plurality of barbs, such as tine 806, disposed in deployed positions between adjacent electrodes. In FIG. 9A, two barbs are shown disposed between adjacent electrodes. However, any number of barbs can be disposed between adjacent electrodes. For example, there can be one, two, three, four, five, six, seven, eight, nine, ten, or more barbs disposed between adjacent electrodes. As will be recognized, other numbers of barbs may also be disposed between adjacent electrodes. In some embodiments, one or more rings of barbs may be disposed between adjacent electrodes. Each ring of barbs may include any number of barbs.

Figure 9B:
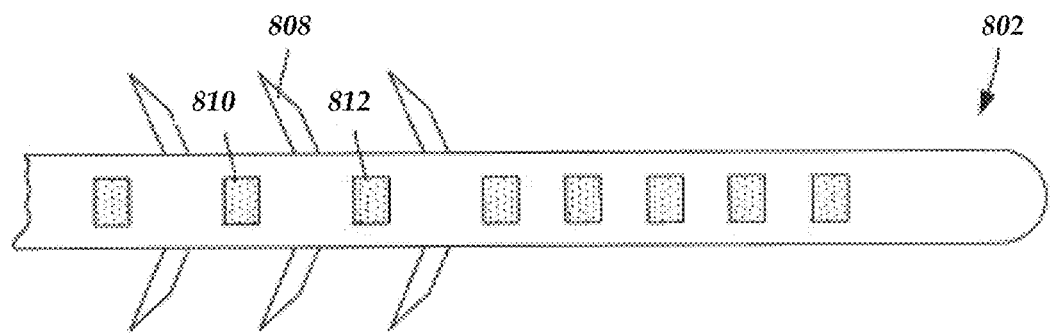
FIG. 9B is a schematic side view of one embodiment of a distal portion of the lead shown in FIG. 9A with barbs in deployed positions disposed between some of a plurality of electrodes, according to the invention.

In alternate embodiments, the barbs are disposed between some adjacent electrodes and are not disposed between other adjacent electrodes. FIG. 9B is a schematic side view of the lead 802 with a tine, such as tine 808, disposed between some adjacent electrodes, such as adjacent electrodes 810 and 812. In at least some embodiments, the barbs shown in FIGS. 9A and 9B can be pivoted between un-deployed positions and deployed positions and adjusted. Additionally, in some embodiments, the barbs shown in FIGS. 9A and 9B can overlap one another while un-deployed.

Figure 9C:
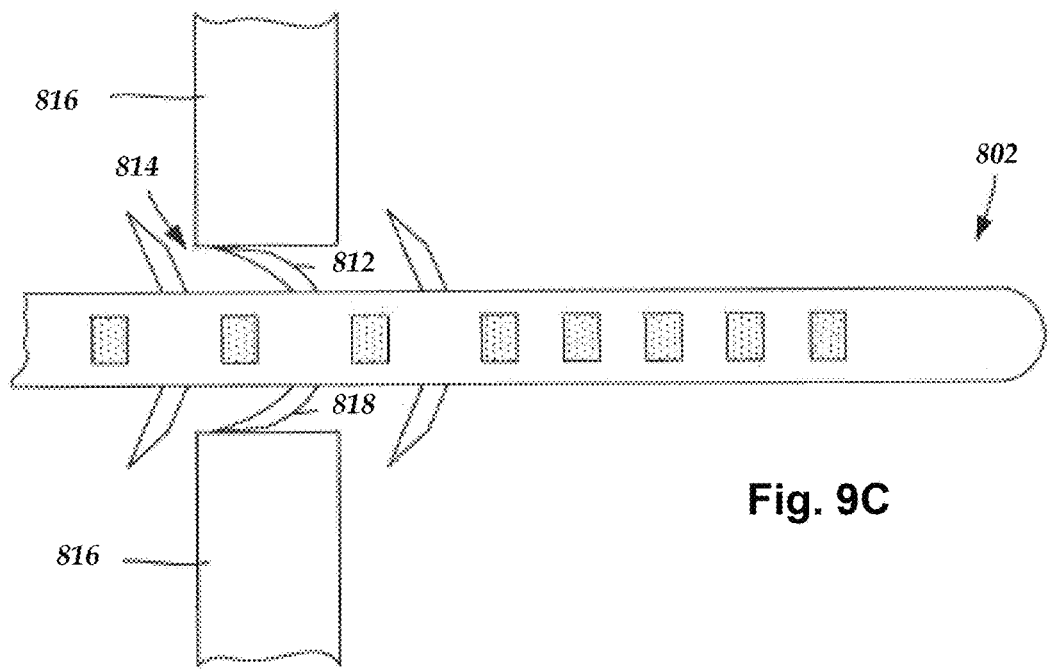
FIG. 9C is a schematic side view of one embodiment of a distal portion of the lead shown in FIG. 9B anchored to the walls of a foramen of a sacrum by barbs disposed in deployed positions between some electrodes at the distal portion of the lead, according to the invention.

FIG. 9C is a schematic side view of one embodiment of the distal portion of the lead 802 extending through a foramen 814 of a bony structure 816. The lead 802 is anchored to the walls of the foramen 814 by barbs disposed in deployed positions between some adjacent electrodes at the distal portion of the lead 802. In some embodiments, the barbs shown in FIGS. 9A and 9B are formed from materials with suitable flexibility to facilitate anchoring within the foramen 814 without damaging nerves and other vessels within the foramen 814. In FIG. 9C, barbs 812 and 818 are shown bent against the walls of the foramen 814. It will be understood that the barbs may be disposed on the lead 802 proximal to or distal to the plurality electrodes in addition to, or instead of, between adjacent electrodes. Once the lead 802 is positioned, re-positioning or subsequent removal of the lead 802 may be facilitated by incorporation of the barbs that can pivot back and forth between deployed and un-deployed positions.

Figure 10A:
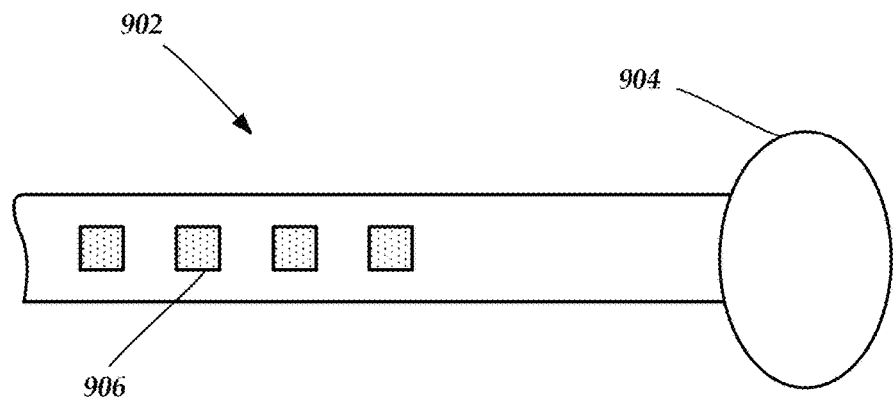
FIG. 10A is a schematic side view of a distal portion of a lead with an balloon-type element disposed on the lead distal to a plurality of electrodes according to an embodiment of the present invention.

In some embodiments, an anchoring unit disposed on a lead includes one or more balloon-type elements that may volumetrically expand. FIG. 10A is a schematic side view of one embodiment of a distal portion of a lead 902 that includes a balloon element 904 disposed in an un-deployed or non-inflated position (not shown) on the lead 902 distal to a plurality of electrodes 906. In at least some embodiments, the lead 902 can be positioned while the balloon element 904 is in the un-deployed position. Once the lead 902 is positioned, the balloon element 904 can be transitioned to a deployed position by expanding or inflating the balloon element 904. In at least some embodiments, the balloon element 904 is permanently or removably coupled to the distal portion of the lead 902. In at least some embodiments, a stylet or other tool disposed in a lumen defined in the lead 902 may be used to maneuver and inflate the balloon element 904.

Figure 10B:
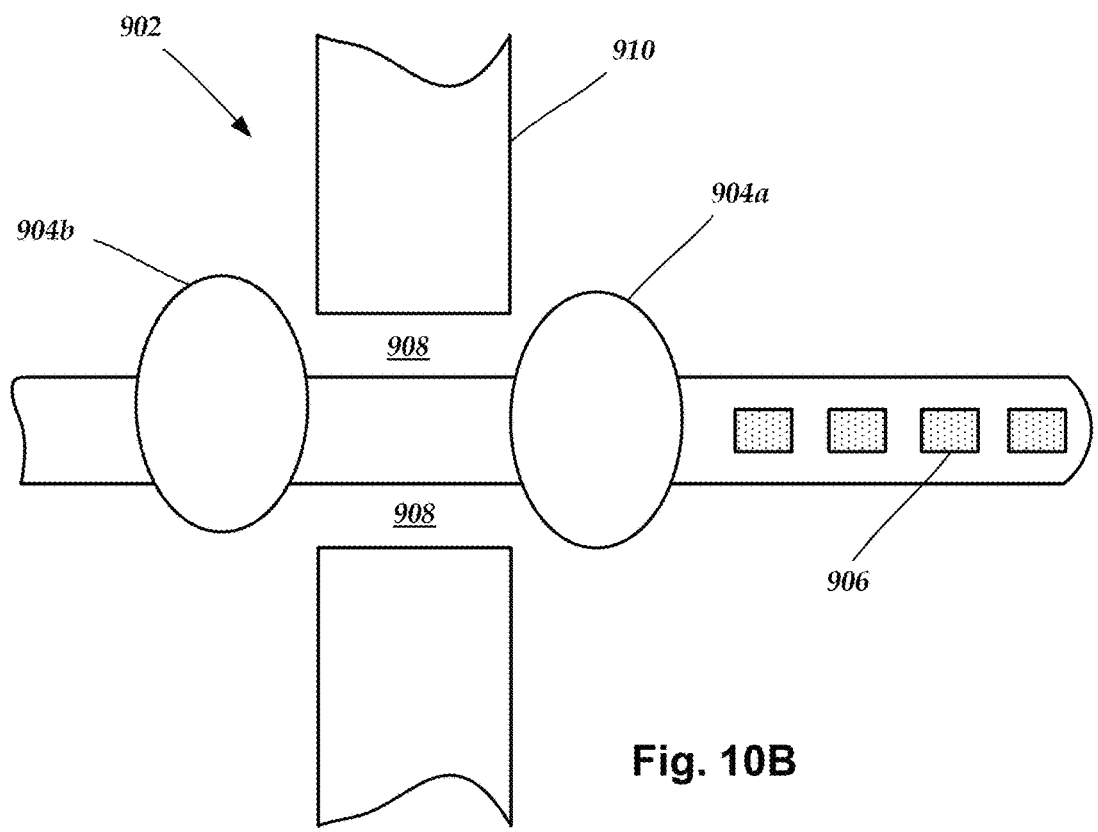
FIG. 10B is a schematic side view of a distal portion of the lead shown in FIG. 10A with two balloon-type elements disposed in a deployed position on the lead distal to the plurality of electrodes according to an embodiment of the present invention.

FIG. 10B is a schematic side view of one embodiment of a distal portion of the lead 902 including two balloon elements 904a, 904b disposed in a deployed position on the lead 902 distal to the plurality of electrodes 906. In at least some embodiments, the balloon elements 904a, 904b are configured and arranged to maintain a deployed position and may be implanted using a lead introducer. In alternate embodiments, the balloon elements 904a, 904b may also be contractible or deflated, so that the balloon elements 904a, 904b can transition from a deployed position to an un-deployed position, and vice-versa. By way of example, the balloon elements 904a, 904b may be deflated for removal.

In at least some embodiments, the balloon elements 904a, 904b can be used to anchor the lead 902 to a bony structure. In at least some embodiments, the distal portion of the lead 902 extends through a foramen 908 of a bony structure 910 and is retained by the bony structure 910 when the balloon elements 904a, 904b are placed in a deployed configuration on the distal portion of the lead 902. The lead 902 extends through the foramen 908 of the bony structure 908 and the balloon elements 904a, 904b are in a deployed configurations on both sides (e.g., distal and proximal sides) of the foramen 908. The balloon elements 904a, 904b each have a diameter, when in the deployed configuration, that is greater than a diameter of the foramen 908. Thus, the balloon elements 904a, 904b prevent the lead 902 from migrating back through the foramen 908 or extending distally further through the foramen 908.

Figure 11A:
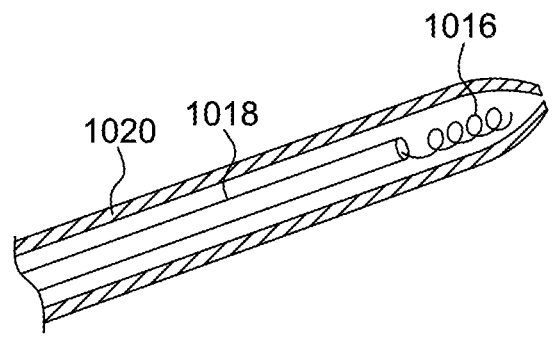
FIG. 11A is a close-up, perspective, cross-sectional view of a coil anchor in an un-deployed configuration according to an embodiment of the present invention.
Figure 11B:
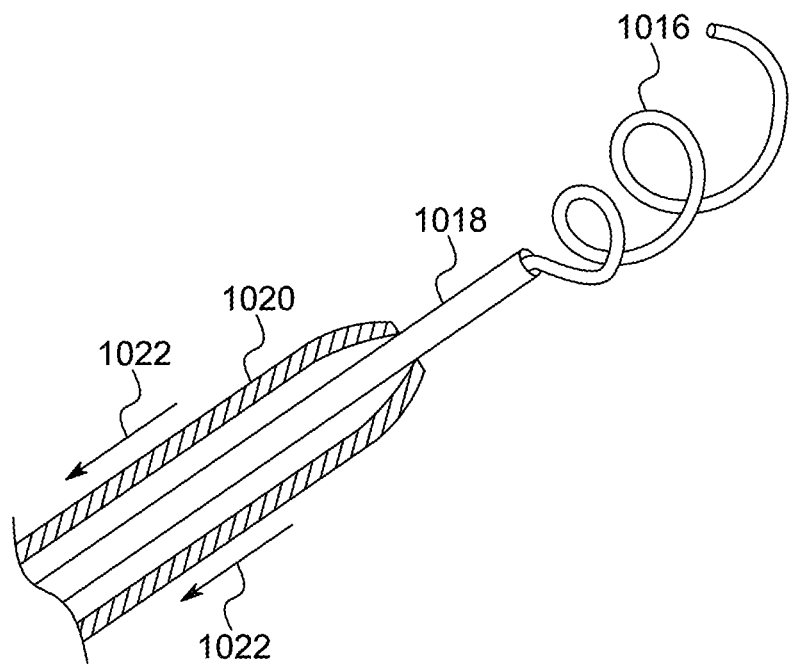
FIG. 11B is a close-up, perspective, cross-sectional view of the coil anchor of FIG. 11C in a deployed configuration according to an embodiment of the present invention.

FIG. 11A schematically shows a coil anchor 1016 in an un-deployed configuration. The coil anchor 1016 is coupled to an anchor introducer 1018, which moves the coil anchor 1016 through a lumen 1020. The coil anchor 1016 remains in the un-deployed configuration as restricted by an inner surface of the lumen 1020. When the coil anchor 1016 is near the DRG (not shown), the anchor introducer 1018 urges the coil anchor 1016 out of the lumen 1020, which permits the coil anchor 1016 to expand into a deployed configuration and intertwine with patient tissue near the DRG. In some embodiments and as illustrated in FIG. 11B, the coil anchor 1016 may take a pigtail shape when in the deployed or expanded configuration. In at least some embodiments, the anchor introducer 1018 can be retracted to pull the coil anchor 1016 back into the lumen 1020 as indicated by arrows 1022.

Figure 12:
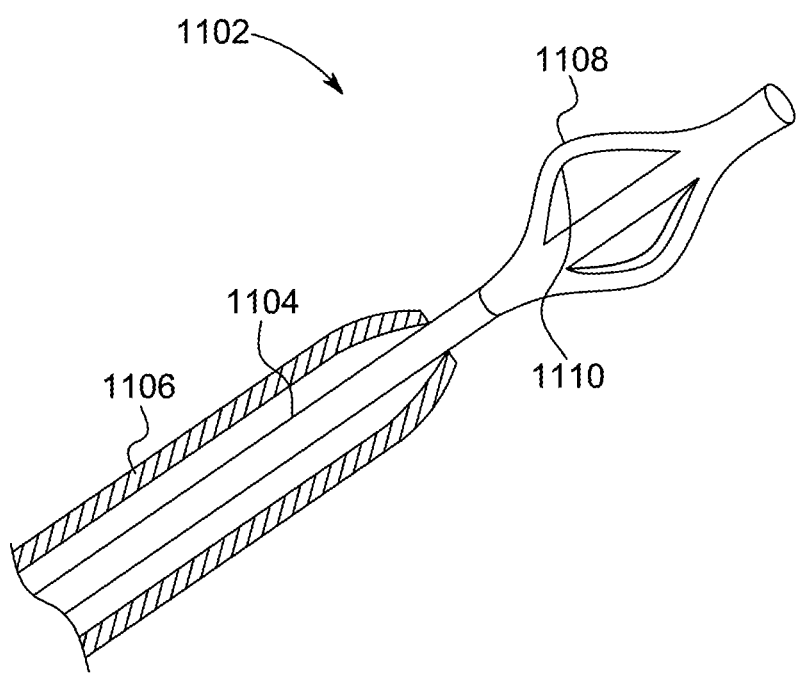
FIG. 12 is a schematic, perspective, cross-sectional view of a malecot anchor according to an embodiment of the present invention.

FIG. 12 schematically shows a malecot anchor 1102 in a deployed configuration. Similar to the coil anchor described above, the malecot anchor 1102 is coupled to an anchor introducer 1104, which moves the malecot anchor 1102 through a lumen 1106. The malecot anchor 1102 is urged through the lumen 1106 in a compressed state, and upon exiting the lumen 1106 expands into a deployed or expanded state, as shown in FIG. 12. In some embodiments, the malecot anchor 1102 takes the form of a self-retaining anchor having two or more flanges 1108 that separate or expand relative to each other when in the deployed configuration. Spaces 1110 between adjacent flanges 1108 permit in-growth of tissue that eventually operates to secure the malecot anchor 1102 near the DRG (not shown).

Figure 13A:
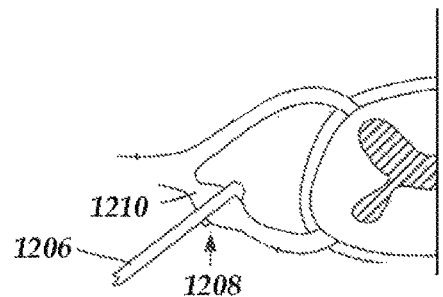
FIG. 13A is a schematic view of a hook-shaped anchor attached to a target anatomy according to an embodiment of the present invention.

FIG. 13A schematically illustrates a lead 1206 having a deployed, hook-shaped end portion 1208 (also see FIG. 13C for close-up view) adaptable to fit around a DRG 1210. In at least some embodiments, the hook-shaped distal end portion extends around at least 40%, 50%, 60%, 70%, 75%, 80%, 90%, 95%, or 100% of the circumference of the DRG 1210. In at least some embodiments and in an un-deployed configuration, the hook-shaped end portion 1208 is initially straight and can be maneuvered by a steering system or guide wire toward the DRG or in a vicinity thereof. Upon reaching its destination, the steering system or guide wire actuates the bending action to generate the hook-shaped end portion 1208.

Figure 13B:
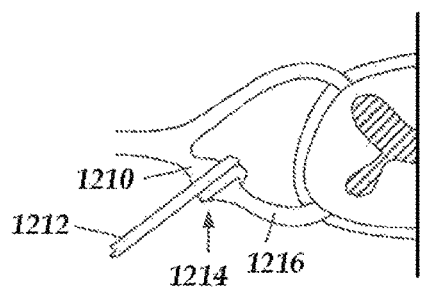
FIG. 13B is a schematic view of a coil-shaped anchor attached to a target anatomy according to an embodiment of the present invention.
Figure 13C:
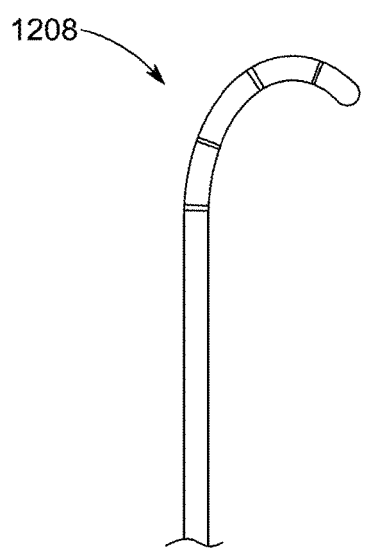
FIG. 13C is a schematic, close-up view of the hook-shaped anchor of FIG. 13A.

FIG. 13B schematically illustrates an embodiment of another lead 1212 having a coil-shaped distal end portion 1214 adaptable to fit around a portion of the DRG 1210. The coil-shaped distal end portion 1214 may include any number of full turns (e.g., 360 degree turns) around the DRG 1210 including, for example, at least one, two, or three full turns. The coil-shaped distal end portion 1214 may also include a partial turn (e.g., less than a 360 degree turn). The turns of the coil-shaped distal end portion 1214 may be situated immediately adjacent to each other in a touching arrangement, or the turns may be separated from each other or any combination thereof.

Figure 13D:
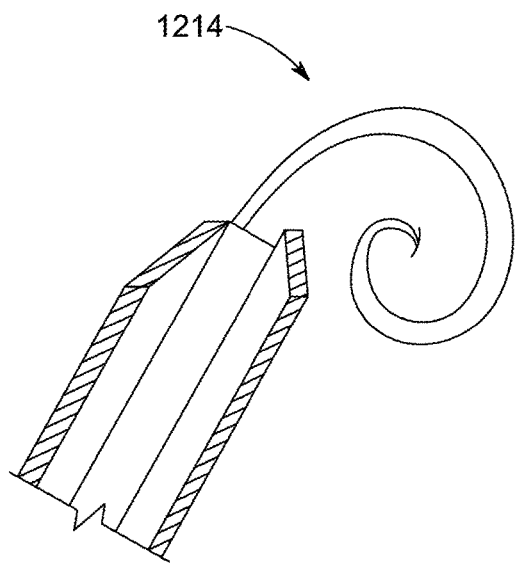
FIG. 13D is a schematic, close-up view of the coil-shaped anchor of FIG. 13B.

In the close-up view of FIG. 13D, the coil-shaped distal end portion 1214 is made from a nitinol wire having a predetermined shape, for example, the nitinol wire may be delivered into the body having one shape and then activated into the coil-shape after implantation.

In at least some embodiments of the arrangements exemplified by FIGS. 13A-13D, the portion of the lead extending from the hook-shaped or coil-shaped distal end portion is arranged to form an angle of at least 45 degrees, 50 degrees, 60 degrees, 70 degrees, 80 degrees, or 85 degrees with a dorsal root 1216. In at least some embodiments, the hook-shaped or coil-shaped distal end portion of the lead body is isodiametric. In at least some embodiments, the hook-shaped or coil-shaped distal end portion of the lead body is also isodiametric with the remainder of the lead. Further description of leads with hook-shaped or coiled-shaped distal end can be found in U.S. Provisional Patent Application No. 61/651,830, which is incorporated herein by reference in its entirety.

Figure 14A:
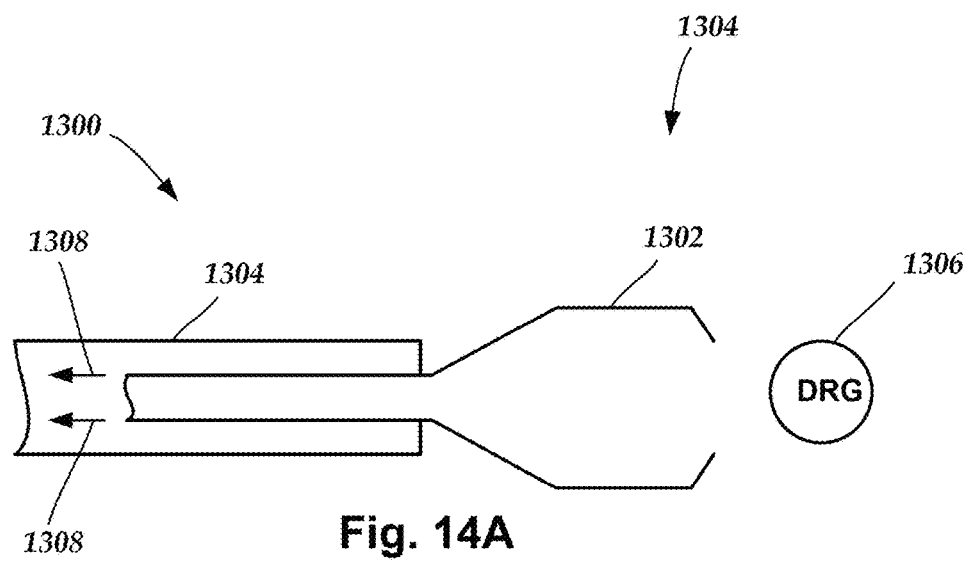
FIG. 14A is a schematic, perspective view of a retention system having a pair of actuatable jaws in an open configuration for capturing a target anatomy according to an embodiment of the present invention.
Figure 14B:
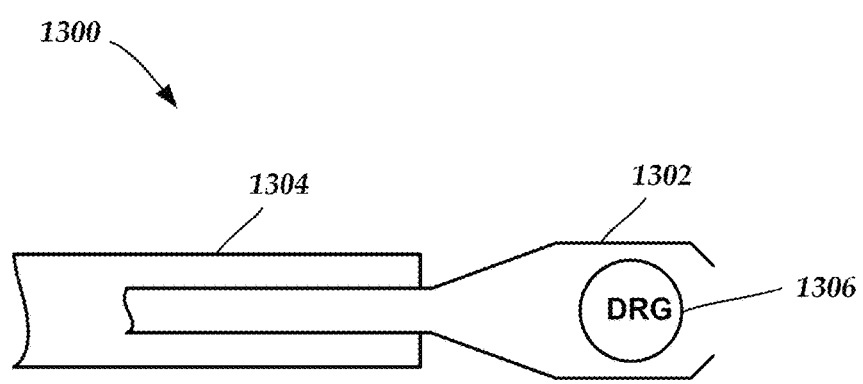
FIG. 14B is a schematic, perspective view of the retention system of FIG. 14A with the actuatable jaws in a closed configuration according to an embodiment of the present invention.

FIG. 14 schematically illustrates a retention system 1300 having an actuatable or movable jaws 1302 extending from a lead 1304. The jaws 1302 are movable to encircle and capture a DRG 1306. In at least some embodiments, the jaws 1302 may have a similar structural form and function as the biasing members and branches described with reference to FIGS. 4-6 in that the jaws 1302 can form a receiving channel to receive the DRG 1306 and a stimulation region to encompass, capture, retain, or surround the DRG 1306. In the present embodiment, the jaws 1302 are controllable to be selectively and remotely manipulated from an un-deployed (implantation) configuration to a deployed (capturing) configuration. For example, the jaws 1302 may held in the un-deployed configuration by applying a force 1308 to the jaws. Once the jaws 1302 are in a target location, the force 1308 may be removed, thus permitting the jaws 1302 to close around the DRG 1306. Additionally or alternatively, the jaws 1302 may be selectively opened and closed at any time during the implantation procedure.

Figure 15:
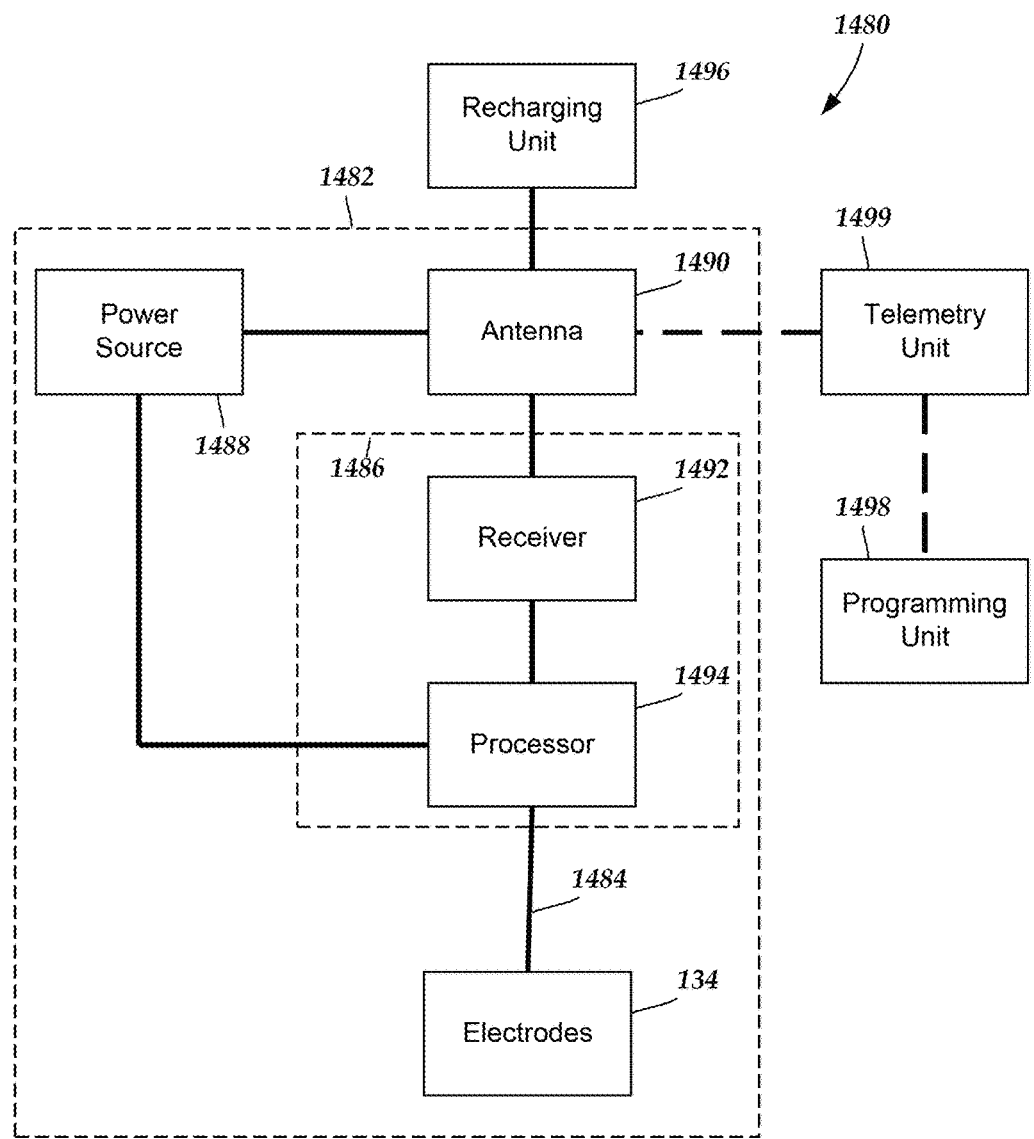
FIG. 15 is a schematic diagram of an electrical stimulation system according to an embodiment of the present invention.

FIG. 15 is a schematic overview of one embodiment of components of an electrical stimulation arrangement 1480 that includes an electrical stimulation system 1482 with a lead 1484, stimulation circuitry 1486, a power source 1488, and an antenna 1490. The electrical stimulation system can be, for example, any of the electrical stimulation systems described above. It will be understood that the electrical stimulation arrangement can include more, fewer, or different components and can have a variety of different configurations including those configurations disclosed in the stimulator references cited herein.

If the power source 1488 is a rechargeable battery or chargeable capacitor, the power source may be recharged/charged using the antenna 1490, if desired. Power can be provided for recharging/charging by inductively coupling the power source 1488 through the antenna 1490 to a recharging unit 1496 external to the user. Examples of such arrangements can be found in the references identified above.

In one embodiment, electrical current is emitted by the electrodes (such as electrodes 134 in FIG. 1) on the lead 1484 to stimulate nerve fibers, muscle fibers, or other body tissues near the electrical stimulation system. The stimulation circuitry 1486 can include, among other components, a processor 1494 and a receiver 1492. The processor 1494 is generally included to control the timing and electrical characteristics of the electrical stimulation system. For example, the processor 1494 can, if desired, control one or more of the timing, frequency, strength, duration, and waveform of the pulses. In addition, the processor 1494 can select which electrodes can be used to provide stimulation, if desired. In some embodiments, the processor 1494 selects which electrode(s) are cathodes and which electrode(s) are anodes. In some embodiments, the processor 1494 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1498 that, for example, allows modification of pulse characteristics. In the illustrated embodiment, the processor 1494 is coupled to a receiver 1492 which, in turn, is coupled to the antenna 1490. This allows the processor 1494 to receive instructions from an external source to, for example, direct the pulse characteristics and the selection of electrodes, if desired.

In one embodiment, the antenna 1490 is capable of receiving signals (e.g., RF signals) from an external telemetry unit 1499 that is programmed by the programming unit 1498. The programming unit 1498 can be external to, or part of, the telemetry unit 1499. The telemetry unit 1499 can be a device that is worn on the skin of the user or can be carried by the user and can have a form similar to a pager, cellular phone, or remote control, if desired. As another alternative, the telemetry unit 1499 may not be worn or carried by the user but may only be available at a home station or at a clinician's office. The programming unit 1498 can be any unit that can provide information to the telemetry unit 1499 for transmission to the electrical stimulation system 1482. The programming unit 1498 can be part of the telemetry unit 1499 or can provide signals or information to the telemetry unit 1499 via a wireless or wired connection. One example of a suitable programming unit is a computer operated by the user or clinician to send signals to the telemetry unit 1499.

The signals sent to the processor 1494 via the antenna 1490 and the receiver 1492 can be used to modify or otherwise direct the operation of the electrical stimulation system 1482. For example, the signals may be used to modify the pulses of the electrical stimulation system such as modifying one or more of pulse duration, pulse frequency, pulse waveform, and pulse strength. The signals may also direct the electrical stimulation system 1482 to cease operation, to start operation, to start charging the battery, or to stop charging the battery.

Optionally, the electrical stimulation system 1482 may include a transmitter (not shown) coupled to the processor 1494 and the antenna 1490 for transmitting signals back to the telemetry unit 1499 or another unit capable of receiving the signals. For example, the electrical stimulation system 1482 may transmit signals indicating whether the electrical stimulation system 1482 is operating properly or not or indicating when the battery needs to be charged or the level of charge remaining in the battery. The processor 1494 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead having a proximal end and a distal end, the lead comprising:
    at the distal end of the lead, a first branch having a first biasing member and a first insulation covering, the first biasing member disposed within the first insulation covering, the first insulation covering having a first inner surface;
    at the distal end of the lead, a second branch having a second biasing member and a second insulation covering, the second biasing member disposed within the second insulation covering, the second insulation covering having a second inner surface,
    wherein the first and second branches define a receiving channel and a stimulation region proximal to the receiving channel,
    wherein the first and second biasing members are, upon application of a force to separate the first and second biasing members, movable away from each other to receive a target anatomy through the receiving channel and, upon removal of the force, are biased to automatically move back toward each other to retain the target anatomy within the stimulation region; and
    at least one electrode disposed on one or both of the first inner surface or the second inner surface, the at least one electrode disposed adjacent to the stimulation region, wherein the at least one electrode is operable to electrically stimulate the target anatomy.

2. The lead of claim 1, wherein the first and second biasing members comprise a shape memory material.

3. The lead of claim 2, wherein the shape memory material is nitinol.

4. The lead of claim 1, wherein at least one of the first or second biasing member is electrically coupled to at least one of the at least one electrode.

5. The lead of claim 1, further comprising a plurality of conductors disposed in one or both of the first or second insulation coverings.

6. The lead of claim 1, wherein the first branch includes a first hook portion.

7. The lead of claim 6, wherein the second branch includes a second hook portion.

8. The lead of claim 7, wherein the first and second hook portions define the receiving channel.

9. An electrical stimulation system comprising:
the lead of claim 1; and
a control module coupleable to the lead, the control module having a housing and an electronic subassembly disposed in the housing.

10. An electrical stimulation lead having a proximal end and a distal end, the lead comprising:
at the distal end of the lead, a first biasing member having a first branch and a second branch extending distally from the first branch;
at the distal end of the lead, a second biasing member having a third branch and a fourth branch extending distally from the third branch,
wherein the second and fourth branches are angled to define a receiving channel and a throat region with a throat width,
wherein the first and third branches define a stimulation region proximal to the receiving channel,
wherein the first and second biasing members are, upon application of a force to separate the first and second biasing members, movable away from each other to increase the throat width and receive a target anatomy through the throat region, and
wherein the first and second biasing members are, upon removal of the force, are biased to automatically move back toward each other to retain the target anatomy within the stimulation region; and
at least one electrode disposed on one or both of the first or second biasing members, the at least one electrode disposed adjacent to the stimulation region, wherein the at least one electrode is operable to electrically stimulate the target anatomy.

11. The lead of claim 10, wherein the first and second biasing members comprise a shape memory material.

12. The lead of claim 11, wherein the shape memory material is nitinol.

13. An electrical stimulation lead having a proximal end and a distal end, the lead comprising, the lead comprising:
a housing located at the distal end of the lead;
an anchor member having a first configuration disposed within the housing;
a lumen coupled to the housing; and
an anchor actuation device extending through the lumen and directly coupled to the anchor member, wherein the anchor actuation device is movable to distally urge the anchor member out of the housing into a deployed configuration in a vicinity of a target anatomy, and wherein the anchor member entangles with patient tissue to secure the lead in the vicinity of the target anatomy.

14. The lead of claim 13, wherein the anchor member is made from nitinol.

15. The lead of claim 13, wherein at anchor member is a ribbon member that is helically wound when in an un-deployed configuration.

16. The lead of claim 13, wherein the anchor member is a coil-shaped anchor member.

17. The lead of claim 16, wherein the coil-shaped anchor member includes a pigtail-shaped configuration when in a deployed configuration.

18. The lead of claim 17, wherein the pigtail-shaped configuration engages a patient's tissue in a vicinity of the target anatomy for neurostimulation.

19. The lead of claim 13 wherein the anchor actuation device is movable to retract the anchor member into an un-deployed configuration.

20. An electrical stimulation system comprising:
the lead of claim 13; and
a control module coupleable to the lead, the control module having a housing and an electronic subassembly disposed in the housing.

* * * * *